US012290249B2

(12) United States Patent
Ma et al.

(10) Patent No.: US 12,290,249 B2
(45) Date of Patent: May 6, 2025

(54) CASE-SPECIFIC FLUID MANAGEMENT

(71) Applicant: Auris Health, Inc., Redwood City, CA (US)

(72) Inventors: Polly Charlene Ma, Fremont, CA (US); Alexander J. Teague, Elmhurst, IL (US); Toni Divic, Stanford, CA (US); Sarah Plewe, Redwood City, CA (US); Mouslim M. Tatarkhanov, Castro Valley, CA (US)

(73) Assignee: Auris Health, Inc., Santa Clara, CA (US)

( * ) Notice: Subject to any disclaimer, the term of this patent is extended or adjusted under 35 U.S.C. 154(b) by 964 days.

(21) Appl. No.: 17/235,619

(22) Filed: Apr. 20, 2021

(65) Prior Publication Data

US 2021/0330309 A1    Oct. 28, 2021

Related U.S. Application Data

(60) Provisional application No. 63/015,853, filed on Apr. 27, 2020.

(51) Int. Cl.
*A61B 17/00* (2006.01)
*A61B 34/30* (2016.01)

(52) U.S. Cl.
CPC ........ *A61B 17/00234* (2013.01); *A61B 34/30* (2016.02); *A61B 2017/00292* (2013.01); *A61B 2034/301* (2016.02); *A61B 2217/005* (2013.01); *A61B 2217/007* (2013.01); *A61B 2560/0487* (2013.01); *A61B 2562/0247* (2013.01)

(58) Field of Classification Search
CPC .............. A61B 17/00234; A61B 34/30; A61B 2034/301; A61B 2017/00292; A61B 2217/005; A61B 2217/007
USPC ........................................................ 604/35
See application file for complete search history.

(56) References Cited

U.S. PATENT DOCUMENTS

| 10,850,013 B2 | 12/2020 | Hsu et al. | |
| 2009/0143642 A1* | 6/2009 | Takahashi | A61B 1/009 600/106 |
| 2015/0119645 A1* | 4/2015 | Baldwin | A61B 17/3462 600/114 |
| 2016/0166320 A1 | 6/2016 | Ciulla et al. | |

(Continued)

OTHER PUBLICATIONS

International search report for appl No. PCTIB2021053262, dated Jul. 12, 2021, 5 pages.

(Continued)

*Primary Examiner* — Phillip A Gray
(74) *Attorney, Agent, or Firm* — Paradice & Li LLP

(57) ABSTRACT

A method of managing fluid conditions in a patient involves advancing at least one medical instrument into a target organ of a patient, the at least one medical instrument comprising an irrigation channel and an aspiration channel, coupling the at least one medical instrument to an irrigation fluid source, providing irrigation from the irrigation fluid source into the target organ through the irrigation channel of the at least one medical instrument, determining an irrigation pressure limit based at least in part on one or more case-specific parameters, providing irrigation into the target organ through the irrigation channel, and limiting the irrigation based at least in part on the determined irrigation pressure limit.

9 Claims, 12 Drawing Sheets

(56) References Cited

U.S. PATENT DOCUMENTS

2018/0289394 A1   10/2018  Shah
2019/0175799 A1*  6/2019  Hsu ................... A61B 17/2202

OTHER PUBLICATIONS

Written Opinion for appl No. PCTIB2021053262, dated Jul. 12, 2021, 7 pages.

* cited by examiner

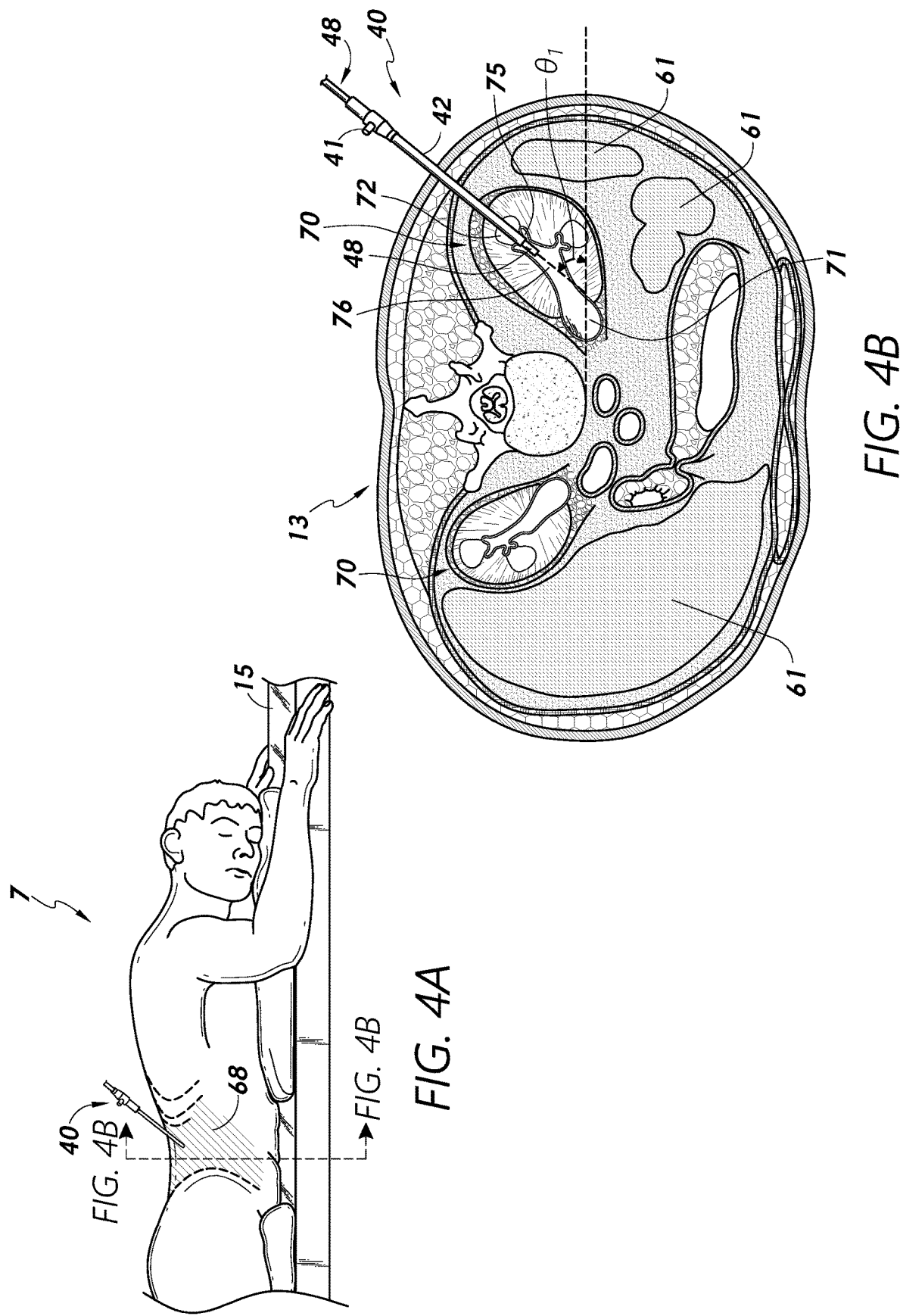

CASE-SPECIFIC FLUID MANAGEMENT

RELATED APPLICATION(S)

This application claims priority to U.S. Provisional Application No. 63/015,853, filed Apr. 27, 2020, and entitled CASE-SPECIFIC FLUID MANAGEMENT, the disclosure of which is hereby incorporated by reference in its entirety.

BACKGROUND

Field

The present disclosure relates to the field of medical procedures.

Description of Related Art

Various medical procedures involve the use of one or more medical instruments for providing fluid irrigation to/from a surgical treatment site, such as an organ, cavity, vessel, or other anatomy of a patient. The improper management of irrigation and/or aspiration in connection with a surgical procedure can adversely affect the health of the patient and/or the efficacy of the procedure.

SUMMARY

Described herein are systems, devices, and methods to facilitate the management of fluid in one or more treatment sites of a patient in connection with certain medical procedures. In particular, fluid management systems, devices, and methods in accordance with one or more aspects of the present disclosure can facilitate fluid management in accordance with certain maximum and/or minimum irrigation pressure/flow limits, which may advantageously be based at least in part on certain case-specific parameter(s). Such parameters may be provided/determined statically and/or dynamically with respect to an operative period during which a medical procedure is performed. Fluid pressure limitation in accordance with aspects of the present disclosure may be implemented in connection with any type of medical procedure involving fluid management, such as nephroscopy or other procedures accessing of the renal anatomy, for example.

In some implementations, the present disclosure relates to a method of managing fluid conditions in a kidney of a patient. The method comprises causing fluidics to be provided between a fluidics source and the kidney of the patient through a fluidics channel of at least one medical instrument disposed at least partially within the kidney, determining a fluid pressure limit based at least in part on one or more case-specific parameters, and limiting the fluidics based at least in part on the determined fluid pressure limit.

The one or more case-specific parameters can comprise one or more of the following parameters: angle of a sheath associated with the at least one medical instrument, amount of aspiration flow, whether active suction is implemented, relative height of the sheath relative to the fluidics source, and patient position. For example, the amount of aspiration flow can be based on a number of passive fluid outflow channels from the kidney through the at least one medical instrument. In some embodiments, the sheath is a percutaneous-access sheath. In some embodiments, the method further comprises determining the angle of the sheath based at least in part on a configuration of a robotic arm holding a catheter disposed at least partially within the at least one medical instrument. The patient position may be one of the group consisting of: prone, supine, modified-supine, and Trendelenburg.

In some embodiments, limiting the fluidics based at least in part on the determined fluid pressure limit maintains internal fluid pressure of the kidney below 33 mmHg. The provision and limiting of the fluidics may distend the kidney without causing damage to the kidney from over pressurization. In some embodiments, the fluid pressure limit is 150 mmHg. Causing fluidics to be provided may involve driving a pump of a fluid control system configured to control a rate of fluid flow from the fluidics source in accordance with the fluid pressure limit.

The method may further comprise determining a presence of a ureteral access sheath at least partially within the kidney, wherein the fluid pressure limit is based at least in part on said determination of the presence of the ureteral access sheath. In some embodiments, the fluidics channel is formed between concentric inner and outer sheaths of the at least one medical instrument. In some embodiments, the at least one medical instrument includes an aspiration channel formed between an inner sheath of the at least one medical instrument and a catheter disposed within the inner sheath. The method can further comprise notifying a user of the fluid pressure limit using a user interface. In some embodiments, the method further comprises determining the one or more case-specific parameters continuously during an operative period and updating the fluid pressure limit in real-time based on the continuously-determined one or more case-specific parameters.

In some implementations, the present disclosure relates to a surgical system comprising a medical instrument assembly including an irrigation channel, a robotic subsystem including one or more articulating arms configured to hold one or more components of the medical instrument assembly, an irrigation source fluidly coupled to the medical instrument assembly, an irrigation control subsystem configured to control a flow of fluid from the irrigation source to the medical instrument assembly, and control circuitry associated with the irrigation control subsystem, the control circuitry being configured to determine an irrigation pressure limit based at least in part on one or more case-specific parameters and control the flow of fluid from the irrigation source to the medical instrument assembly in accordance with the irrigation pressure limit.

The one or more case-specific parameters comprise one or more of the following parameters: angle of a sheath associated with the medical instrument assembly, amount of aspiration flow, whether active suction is implemented, relative height of the sheath relative to the irrigation source, and patient position. In some embodiments, the irrigation channel is formed between inner and outer sheaths of a percutaneous-access instrument of the medical instrument assembly and the one or more components comprises a catheter configured to be disposed at least partially within the inner sheath of the percutaneous-access instrument. In some embodiments, the control circuitry is further configured to determine an angle of a distal portion of one of the one or more articulating arms and one of the one or more case-specific parameters is based on the angle.

In some embodiments, the medical instrument assembly includes an active suction lumen and the one or more case-specific parameters indicate a status of the active suction lumen. The system can further comprise an electronic display, wherein the control circuitry is further configured to present, using the electronic display, a graphical user interface indicating a pressure range having an upper limit at the irrigation pressure limit. The control circuitry may be further configured to determine the one or more case-specific parameters continuously during an operative period and update the irrigation pressure limit continuously during the operative period based at least in part on the continuously-determined one or more case-specific parameters. In some embodiments, the irrigation source comprises a bag of fluid coupled to a support structure and the one or more case-specific parameters indicate a height of at least one of the bag of fluid and a portion of the support structure relative to a height of one or more components of the medical instrument assembly. In some embodiments, the medical instrument assembly includes one or more pressure sensors configured to be disposed in a target organ of a patient and the one or more case-specific parameters indicate a pressure of the target organ based at least in part on a signal from the one or more pressure sensors.

In some implementations, the present disclosure relates to a fluid control device comprising a flow control device configured to control a flow of fluid from an irrigation fluid source and control circuitry comprising one or more processors and one or more data storage devices. The control circuitry is configured to access one or more case-specific parameters stored in the one or more data storage devices, determine an irrigation pressure limit based at least in part on the one or more case-specific parameters, and transmit one or more signals to the flow control device to thereby cause the flow control device to control the flow of fluid from the irrigation fluid source in accordance with the irrigation pressure limit. The one or more case-specific parameters may indicate positions of one or more actuators of a surgical robotic device. In some embodiments, the flow control device is one of a fluid pump and a fluid valve.

In some implementations, the present disclosure relates to a method of fluid management. The method comprises receiving case-specific parameter data relating to fluid pressure in a target organ of a patient, determining a case-specific irrigation pressure limit based at least in part on the case-specific parameter data, generating user interface data representing a user interface indicating the case-specific irrigation pressure limit, and transmitting the user interface data to an electronic display to thereby cause the user interface to be displayed to a user.

In some embodiments, the user interface data further represents an active suction level applied to the target organ. The method may further comprise determining that an irrigation pressure associated with the target organ exceeds a predetermined threshold and generating additional user interface data representing a limit-overwrite interface querying the user as to whether the user wishes to overwrite the case-specific irrigation pressure limit. In some embodiments, the case-specific parameter data is manually-input parameter data.

For purposes of summarizing the disclosure, certain aspects, advantages and novel features have been described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

FIGS. 4A and 4B show side and cross-sectional views, respectively, of a patient in a prone position having a percutaneous-access system disposed at least partially in his/her renal anatomy in accordance with one or more embodiments.

DETAILED DESCRIPTION

Figure 1:
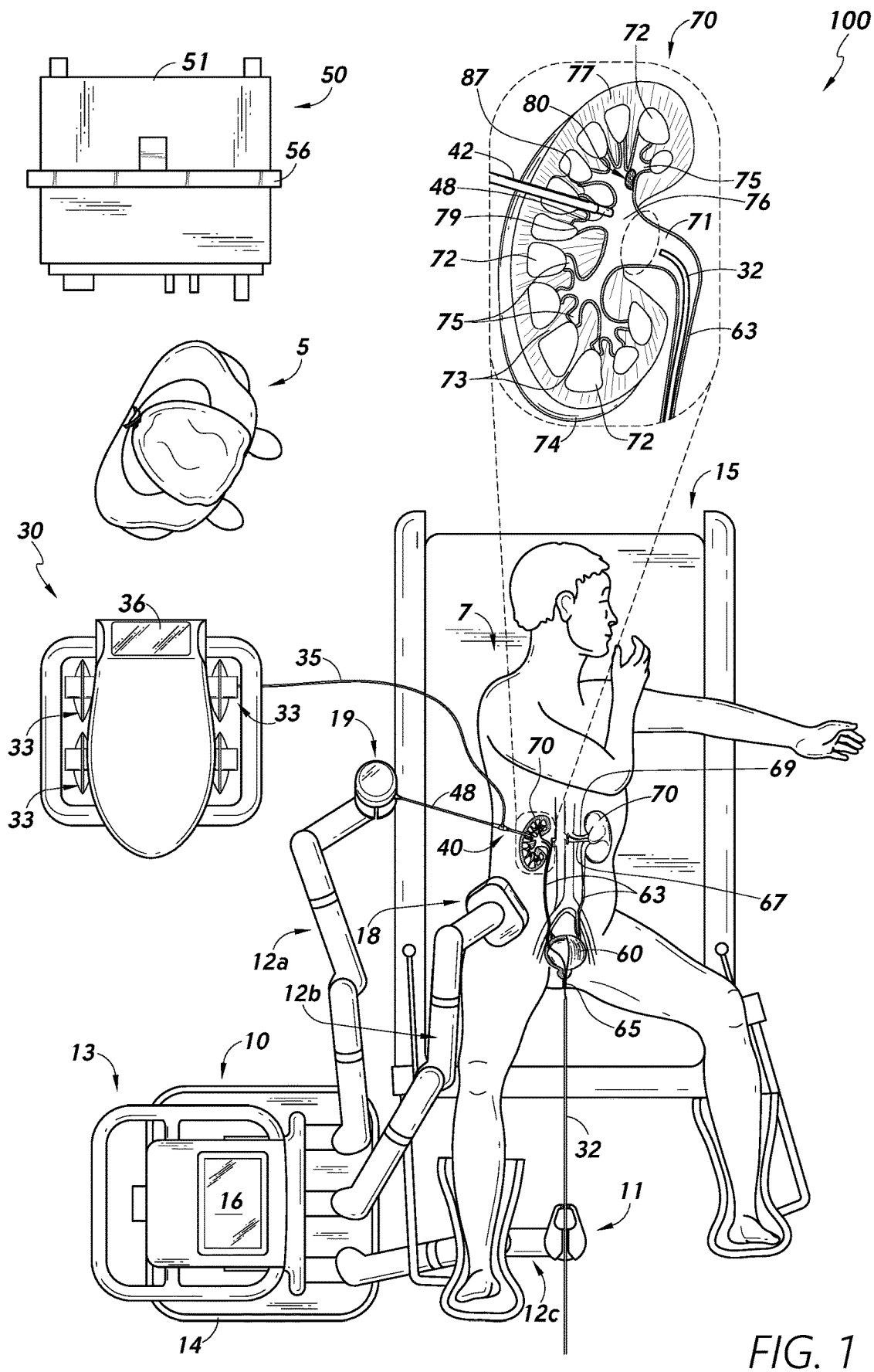
FIG. 1 illustrates an embodiment of a medical system including one or more fluid-management components in accordance with one or more embodiments.

The headings provided herein are for convenience only and do not necessarily affect the scope or meaning of the claimed invention. Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain standard anatomical terms of location are used herein to refer to the anatomy of animals, and namely humans, with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Overview

The present disclosure relates to systems, devices, and methods for managing fluid pressures in medical instruments and/or patient anatomy, such as during execution of a medical procedure. Although certain aspects of the present disclosure are described in detail herein in the context of renal, urological, and/or nephrological procedures, such as kidney stone removal/treatment procedures, it should be understood that such context is provided for convenience and clarity, and irrigation fluid management and irrigation fluid pressure limitation concepts disclosed herein are applicable to any suitable medical procedures. However, as mentioned, description of the renal/urinary anatomy and associated medical issues and procedures is presented below to aid in the description of the inventive concepts disclosed herein.

Kidney stone disease, also known as urolithiasis, is a medical condition that involves the formation in the urinary tract of a solid piece of material, referred to as "kidney stones," "urinary stones," "renal calculi," "renal lithiasis," or "nephrolithiasis." Urinary stones may be formed and/or found in the kidneys, the ureters, and the bladder (referred to as "bladder stones"). Such urinary stones can form as a result of mineral concentration in urinary fluid and can cause significant abdominal pain once such stones reach a size sufficient to impede urine flow through the ureter or urethra. Urinary stones may be formed from calcium, magnesium, ammonia, ur acid, cysteine, and/or other compounds or combinations thereof.

Generally, there are several methods for treating patients with kidney stones, including observation, medical treatments (such as expulsion therapy), non-invasive treatments (such as extracorporeal shock wave lithotripsy (ESWL), and surgical treatments (such as ureteroscopy and percutaneous nephrolithotomy ("PCNL"); see description below for details). In surgical approaches (e.g., ureteroscopy and PCNL), the physician gains access to the pathology (i.e., the object to be removed; e.g., the stone), the stone is broken into smaller pieces or fragments, and the relatively small stone fragments/particulates are mechanically extracted from the kidney.

To remove urinary stones from the bladder and ureter, surgeons may insert a ureteroscope into the urinary tract through the urethra. Typically, a ureteroscope includes an endoscope at its distal end configured to enable visualization of the urinary tract. The ureteroscope can also include a lithotripsy device to capture or break apart urinary stones. During a ureteroscopy procedure, one physician/technician may control the position of the ureteroscope, while another other physician/technician may control the lithotripsy device(s).

In order to remove relatively large stones from the kidneys (i.e., "kidney stones"), physicians may use a percutaneous nephrolithotomy ("PCNL") technique that involves inserting a nephroscope through the skin (i.e., percutaneously) and intervening tissue to provide access to the treatment site for breaking-up and/or removing the stone(s). A percutaneous access instrument (e.g., nephroscope, sheath, and/or catheter) used to provide an access channel to the target anatomical site (and/or a direct-entry endoscope) may include one or more fluid channels for providing irrigation fluid flow to the target site and/or aspirating fluid from the target site (e.g., through passive outflow and/or active suction). Generally, the efficacy of percutaneous access to a target calyx and/or direct access to the target calyx through the urinary system can depend at least in part on the fluid conditions (e.g., fluid volume and/or pressure levels) within the kidney. Such conditions can depend at least in part on the fluid management provided using the fluid channel(s), wherein such fluid management is directed at least in part by certain control circuitry associated with one or more devices/systems implemented in a medical procedure. During PCNL, fluidics can be applied to clear stone dust, small fragments, and thrombus from the treatment site as well as the visual field provided by the medical instruments.

Robotic-assisted percutaneous procedures can be implemented in connection with various medical procedures, such as kidney stone removal procedures, wherein robotic tools can enable a physician/urologist to perform endoscopic (e.g., ureteroscopy) target access as well as percutaneous access/treatment. Advantageously, aspects of the present disclosure relate to systems, devices, and methods for limiting irrigation fluid pressure levels with respect to maximum and/or minimum pressure levels associated with certain medical instruments and/or patient treatment sites/anatomy.

In several of the examples described herein, object removal procedures relate to removal of kidney stones from a kidney. This disclosure, however, is not limited only to kidney stone removal. For example, the following description is also applicable to other surgical or medical operations or medical procedures concerned with the removal of objects from a patient, including any object that can be removed from a treatment site or patient cavity (e.g., the esophagus, ureter, intestine, eye, etc.) via percutaneous and/or endoscopic access, such as, for example, gallbladder stone removal, lung (pulmonary/transthoracic) tumor biopsy, or cataract removal. Furthermore, although aspects of the present disclosure are described herein for convenience in the context of nephroscopic operations, it should be understood that inventive aspects of the present disclosure may be implemented in any suitable or desirable type of percutaneous and/or endoscopic medical procedure, whether robotic or not.

Medical System

FIG. 1 illustrates an example medical system 100 for performing various medical procedures in accordance with aspects of the present disclosure. The medical system 100 may be used for, for example, percutaneous and/or endoscopic (e.g., ureteroscopic) procedures. As referenced and described above, certain ureteroscopic procedures involve the treatment/removal of kidney stones. In some implementations, kidney stone treatment can benefit from the assistance of certain robotic technologies/devices, such as may be similar to those shown in FIG. 1 and described in detail below. Robotic medical solutions can provide relatively higher precision, superior control, and/or superior hand-eye coordination with respect to certain instruments compared to strictly-manual procedures. For example, robotic-assisted percutaneous access to the kidney in accordance with some procedures can advantageously enable a urologist to perform both direct-entry endoscopic renal access and percutaneous renal access.

In certain stone management procedures, fluid irrigation may be implemented in order to maintain desired kidney distention, which may advantageously facilitate visualization and/or navigation within the target treatment site (e.g., calyx networks of kidney). However, it may be desirable or necessary to limit fluid irrigation at least in part to avoid over-pressurizing the kidney, which can result in physiological harm to the patient and/or damage to the renal anatomy. Specifically, with respect to renal procedures, over-pressurization can result in fractures, tissue breakage, and/or other physical damage. Furthermore, in the presence of active infection, fluid can be dispersed into the bloodstream in response to such breakage, possibly resulting in sepsis, fever, and/or other condition(s). For example, intrarenal infection may result from the presence of one or more kidney stones. Therefore, infected intrarenal fluid that is expelled or otherwise passes into the bloodstream as a result of damage from over-pressurization can result in complications as described above. Therefore, it may be desirable to limit irrigation pressure levels in order to promote the desired/sufficient kidney distention to perform a stone management procedure without causing undesirably high intrarenal pressures. Furthermore, under-pressurization can result in the lack of effective anatomical distention for visualization, which can reduce the efficacy of a procedure and/or result in damage to the internal anatomy.

In order to operate within suitable or desirable irrigation pressure ranges, embodiments of the present disclosure provide for the implementation/enforcement of maximum (and/or minimum) irrigation pressure limits with respect to irrigation sources used in connection with relevant medical procedures. Although a human patient 7 is shown, it should be understood that principles disclosed herein are applicable to veterinary procedures as well and animal patients. According to some solutions, irrigation limits are based on a procedure type. For example, different irrigation limits may be associated with ureteroscopy, PCNL, cystoscopy, hysteroscopy, and/or other procedures. Such limits may further be based at least in part on the types of devices used in connection with the particular procedure.

Limits on irrigation pressures/flow may be a result of physical limits, such as the height of irrigation fluid source(s) (e.g., IV pole), or they may be driven/enforced by control signals implemented using system control circuitry. For example, a fluid management system may maintain irrigation limit values and/or enforce the same. Generally, for safety purposes, irrigation limits may be set such that a sufficiently high percentage of cases for a given procedure fall under the pressure limit(s) associated with the maximum intrarenal pressure. However, where irrigation limits do not incorporate case-specific parameters/inputs, the limits may generally err on the side of lower with respect to maximum irrigation limits or higher or minimum irrigation limits to ensure that a sufficient portion of cases fall within the proscribed pressure limit(s). Therefore, such systems may often fail to meet or take advantage of ideal intrarenal pressures that may fall outside of conservative pressure limit ranges but may nevertheless be objectively safe in a specific case. Therefore, irrigation limits and solutions that do not incorporate case-specific parameter data/inputs can result in insufficient anatomical distention and/or safety conditions being compromised.

Although some embodiments of the present disclosure are presented in the context of nephroscopes, ureteroscopes and/or human renal anatomy, it should be understood that the principles disclosed herein may be implemented in any type of endoscopic and/or percutaneous procedure. Furthermore, several of the examples described herein relate to object removal procedures involving the removal of kidney stones from a kidney. The present disclosure, however, is not limited only to kidney stone removal. For example, the following description is also applicable to other surgical or medical operations or medical procedures concerned with the removal of objects from a patient, including any object that can be removed from a treatment site or patient cavity (e.g., the esophagus, ureter, intestine, eye, etc.) via percutaneous and/or endoscopic access, such as, for example, gallbladder stone removal, lung (pulmonary/transthoracic) tumor biopsy, or cataract removal.

The medical system 100 includes a robotic system 10 (e.g., mobile robotic cart) configured to engage with and/or control a medical instrument 32 (e.g., ureteroscope) to perform a direct-entry procedure on a patient 7. The term "direct-entry" is used herein according to its broad and ordinary meaning and may refer to any entry of instrumentation through a natural or artificial opening in a patient's body. For example, with reference to FIG. 1, the direct-entry of the scope 32 into the urinary tract of the patient 7 may be made via the urethra 65.

In the illustrated system 100, a percutaneous-access instrument 40 is further implemented to provide percutaneous access to the kidney 70. The percutaneous-access instrument 40 may include one or more sheaths and/or shafts through which instruments and/or fluids may access the target anatomy in which the distal end of the instrument 40 is disposed. The term "percutaneous access" is used herein according to its broad and ordinary meaning and may refer to entry, such as by puncture and/or minor incision, of instrumentation through the skin of a patient and any other body layers necessary to reach a target anatomical location associated with a procedure (e.g., the calyx network of the kidney 70). The term "percutaneous-access instrument" is used herein according to its broad and ordinary meaning and may refer to a surgical tool, device, or assembly that is configured to puncture or to be inserted through skin and/or other tissue/anatomy, such as a needle, a scalpel, a guidewire, sheath, shaft, scope, and the like. However, it should be understood that a percutaneous-access instrument can refer to other types of medical instruments in the context of the present disclosure. Although described in some contexts herein as a nephroscope and an endoscope, respectively, it should be understood that the percutaneous-access instruments 40, 48 and direct-entry instrument 32 may be any type of medical instruments, including endoscopes (such as a ureteroscope), catheters (such as a steerable or non-steerable catheter), a nephroscopes, laparoscopes, or other type of medical instrument.

The system 100 may include a catheter 48, which may access the internal renal anatomy through the percutaneous-access instrument 40. In some embodiments, the catheter 48 may be manipulated and/or held in place by a tool/coupling 19 coupled to an arm 12a of the robotic system 10. The catheter 48 may be a flexible, robotically-driven instrument. In some embodiments, an aspiration outflow channel may be formed in the space between the outer wall of the catheter 48 and an inner wall/sheath of the percutaneous-access device/assembly 40, wherein the catheter 48 is disposed within a channel formed by such inner wall/sheath. With the catheter 48 disposed within the percutaneous-access instrument 40, the catheter 48 and the shaft(s)/sheath(s) of the percutaneous-access instrument 40 may be generally concentric. The catheter 48 and the percutaneous access instrument 40 may advantageously have generally circular cross-sectional shape over at least a portion thereof.

In some embodiments, the percutaneous access instrument/assembly 40 and/or other of the medical instruments of the system 100 form or provide multiple passive fluid outflow channels. For example, passive outflow channels may include a channel formed between the outer wall of the scope 32 and an access sheath through which the scope 32 is passed/disposed. As another example, a working channel of the scope 32 may provide a passive aspiration outflow path from the kidney 70. In some embodiments, active outflow is provided through the percutaneous catheter 48 (i.e., active suction). In cases in which active suction is not implemented within the percutaneous catheter 48, passive aspiration outflow may flow therethrough to some degree. In some configurations, the greatest volume of passive aspiration outflow may be between the outside of the catheter 48 and the inner wall/sheath of the percutaneous-access instrument/assembly 40.

The medical system 100 also includes a fluid management cart 30, which may be configured to hold one or more fluid bags/containers 33 and/or control fluid flow therefrom. For example, an irrigation line 35 may be coupled to one or more of the bags/containers 33 and to an irrigation port of the percutaneous-access instrument/assembly 40. Irrigation fluid may be provided to the target anatomy via the irrigation line 35 and the percutaneous-access instrument/assembly 40. The fluid management cart 30 may include certain electronic components, such as a display 36, flow control mechanics, and/or certain associated control circuitry.

The fluid management cart 30 may comprise a stand-alone tower/cart and may have one or more IV bags 33 hanging on one or more sides thereof. The cart 30 may include a pump with which aspiration fluid may be pulled into a collection container/cartridge. In some embodiments, the irrigation fluid pressure is determined at least in part by the height of the pressure sensor in the fluid management cart 30. That is, the pressure level of the irrigation fluid may be determined with respect to one or more points along the irrigation and/or aspiration fluid channel(s). Such fluid pressure may be set to various setpoints that are limited in some respect by irrigation fluid pressure limits determined based on case-specific criteria, as described in detail herein.

The medical system 100 also includes a control system 50 configured to interface with the robotic system 10 and/or fluid cart 30, provide information regarding the procedure, and/or perform a variety of other operations. For example, the control system 50 can include one or more display(s) 56 configured to present certain information to assist the physician 5 and/or other technician(s) or individual(s). The medical system 10 can include a table 15 configured to hold the patient 7. The system 10 may further include an electromagnetic (EM) field generator 18, which may be held by one or more of the robotic arms 12 of the robotic system 10 or may be a stand-alone device. Although the various robotic arms are shown in various positions and coupled to various instrumentation, it should be understood that such configurations are shown for convenience and illustration purposes, and such robotic arms may have different configurations over time and/or at different points during a medical procedure. In some embodiments, the arm 12a is configured to hold/control the catheter 48 only after removing the electromagnetic field generator 18 therefrom. That is, the instrument coupling 19 and the field generator 18 may generally be mounted to the same robotic arm as interchanged over time.

In some implementations, the system 100 may be used to perform a percutaneous procedure, such as percutaneous nephrolithotomy (PCNL). To illustrate, if the patient 7 has a kidney stone 80 that is too large to be removed/passed through the urinary tract (63, 60, 65), the physician 5 can perform a procedure to remove the kidney stone 80 through a percutaneous access point/path associated with the flank/side of the patient 7. In some embodiments, the physician 5 can interact with the control system 50 and/or the robotic system 10 to cause/control the robotic system 10 to advance and navigate the medical instrument 32 (e.g., a scope) from the urethra 65, through the bladder 60, up the ureter 63, and into the calyx network of the kidney 70 where the stone 80 is located. The physician 5 can further interact with the control system 50 and/or the robotic system 10 to cause/control the advancement of the catheter 48 through the percutaneous-access instrument 40. The control system 50 can provide information via the display(s) 56 that is associated with the medical instrument 32, such as real-time endoscopic images captured therewith, and/or other instruments of the system 100, to assist the physician 5 in navigating/controlling such instrumentation.

The renal anatomy is described herein for reference with respect to certain medical procedures relating to aspects of the present inventive concepts. The kidneys 70, shown roughly in typical anatomical position in FIG. 1, generally comprise two bean-shaped organs located on the left and right sides, respectively, in the retroperitoneal space. In adult humans, the kidneys are generally about 11 cm in height/length. The kidneys receive blood from the paired renal arteries 69; blood exits the kidney via the paired renal veins 67. Each kidney 70 is fluidly coupled with a respective ureter 63, which generally comprises a tube that carries excreted urine from the kidney 70 to the bladder 60.

The kidneys 70 are typically located relatively high in the abdominal cavity and lie in a retroperitoneal position at a slightly oblique angle. The asymmetry within the abdominal cavity, generally caused by the position of the liver, results in the right kidney (shown in detail in FIG. 1) typically being slightly lower and smaller than the left, and being placed slightly more to the middle than the left kidney. On top of each kidney is an adrenal gland (not shown). The upper parts of the kidneys 70 are partially protected by the 11th and 12th ribs (not shown). Each kidney, with its adrenal gland, is generally surrounded by two layers of fat: the perirenal fat present between renal fascia and renal capsule and pararenal fat superior to the renal fascia.

The kidneys 70 participate in the control of the volume of various body fluid compartments, fluid osmolality, acid-base balance, various electrolyte concentrations, and removal of toxins. The kidneys 70 provide filtration functionality by secreting certain substances and reabsorbing others. Examples of substances secreted into the urine are hydrogen, ammonium, potassium and uric acid. In addition, the kidneys also carry out various other functions, such as hormone synthesis, and others.

A recessed area on the concave border of the kidney 70 is the renal hilum 78, where the renal artery (not shown in the detailed view of the kidney 70) enters the kidney 70 and the renal vein (not shown in detailed view) and ureter 63 leave. The kidney 70 is surrounded by tough fibrous tissue, the renal capsule 74, which is itself surrounded by perirenal fat, renal fascia, and pararenal fat. The anterior (front) surface of these tissues is the peritoneum, while the posterior (rear) surface is the *transversalis* fascia.

The functional substance, or parenchyma, of the kidney 70 is divided into two major structures: the outer renal cortex 77 and the inner renal medulla 87. These structures take the shape of a plurality of generally cone-shaped renal lobes, each containing renal cortex surrounding a portion of medulla called a renal pyramid 72. Between the renal pyramids 72 are projections of cortex called renal columns 73. Nephrons (not shown in detail in FIG. 1), the urine-producing functional structures of the kidney, span the cortex 77 and medulla 87. The initial filtering portion of a nephron is the renal corpuscle, which is located in the cortex and is followed by a renal tubule that passes from the cortex deep into the medullary pyramids. Part of the renal cortex, a medullary ray, is a collection of renal tubules that drain into a single collecting duct.

The tip/apex, or papilla 79, of each renal pyramid empties urine into a respective minor calyx 75; minor calyces 75 empty into major calyces 76, and major calyces 76 empty into the renal pelvis 71, which transitions to the ureter 63. The manifold-type collection of minor and major calyces may be referred to herein as the "calyx network" of the kidney. At the hilum 78, the ureter 63 and renal vein exit the kidney and the renal artery enters. Hilar fat and lymphatic tissue with lymph nodes surrounds these structures. The hilar fat is contiguous with a fat-filled cavity called the renal sinus. The renal sinus collectively contains the renal pelvis 71 and calyces 75, 76 and separates these structures from the renal medullary tissue. The funnel/tubular-shaped anatomy associated with the calyces can be referred to as the infundibulum/infundibula. That is, an infundibulum generally leads to the termination of a calyx where a papilla is exposed within the calyx.

With further reference to the medical system 100, the medical instrument 32 (e.g., scope, directly-entry instrument, etc.) can be advanced into the kidney 70 through the urinary tract. Once at the site of the kidney stone 80 (e.g., within a target calyx 75 of the kidney 70 through which the stone 80 is accessible), the medical instrument 32 can be used to designate/tag a target location for percutaneous access to the kidney 70. To minimize damage to the kidney and/or surrounding anatomy, the physician 5 can designate a particular papilla 79 of the kidney 70 as the target location/anatomical feature for entering into the kidney 70 with a percutaneous-access instrument (e.g., needle). However, other target locations can be designated or determined. Once the percutaneous-access instrument(s) has/have reached the target location (e.g., calyx 75), the utilized percutaneous access path may be used to extract the kidney stone 80 from the patient 7.

Fluid may advantageously be directed into the calyx network using the fluid cart 30 and irrigation line 35 throughout at least portions of the procedure to produce desirable kidney distension for navigation and viewing. In cases of under-pressurization, wherein there is not enough fluid in the kidney to produce desired or necessary distention, laser lithotripsy, can result in accidental damage to tissue at the treatment site by the laser as a result of the collapse of the surrounding anatomy from under-pressurization.

In the example of FIG. 1, the medical instrument 32 is implemented as a scope. However, the medical instrument 32 can each be implemented as any suitable type of medical instrument, such as a catheter, a guidewire, a lithotripter, a basket retrieval device, and so on. In some embodiments, the medical instrument 32 is a steerable device.

The various scope-type instruments disclosed herein, such as the scope 32 of the system 100, can be configured to navigate within the human anatomy, such as within a natural orifice or lumen of the human anatomy. The terms "scope" and "endoscope" are used herein according to their broad and ordinary meanings, and may refer to any type of elongate medical instrument having image generating, viewing, and/or capturing functionality and configured to be introduced into any type of organ, cavity, lumen, chamber, or space of a body. A scope can include, for example, a ureteroscope (e.g., for accessing the urinary tract), a laparoscope, a nephroscope (e.g., for accessing the kidneys), a bronchoscope (e.g., for accessing an airway, such as the bronchus), a colonoscope (e.g., for accessing the colon), an arthroscope (e.g., for accessing a joint), a cystoscope (e.g., for accessing the bladder), colonoscope (e.g., for accessing the colon and/or rectum), borescope, and so on. Scopes/endoscopes, in some instances, may comprise a rigid or flexible tube, and may be dimensioned to be passed within an outer sheath, catheter, introducer, or other lumen-type device, or may be used without such devices.

Irrigation fluid may be provided to the treatment site (e.g., kidney 70) through the percutaneous-access device 40, through the percutaneous-access catheter 48, and/or through the direct-entry device 32. Furthermore, irrigation and aspiration may or may not be provided through the same instrument(s). Where one or more of the instruments (32, 40, 48) provides the irrigation and/or aspiration functionality, one or more others of the instruments may be used for other functionality, such as breaking-up the object 80 to be removed.

Figure 2:
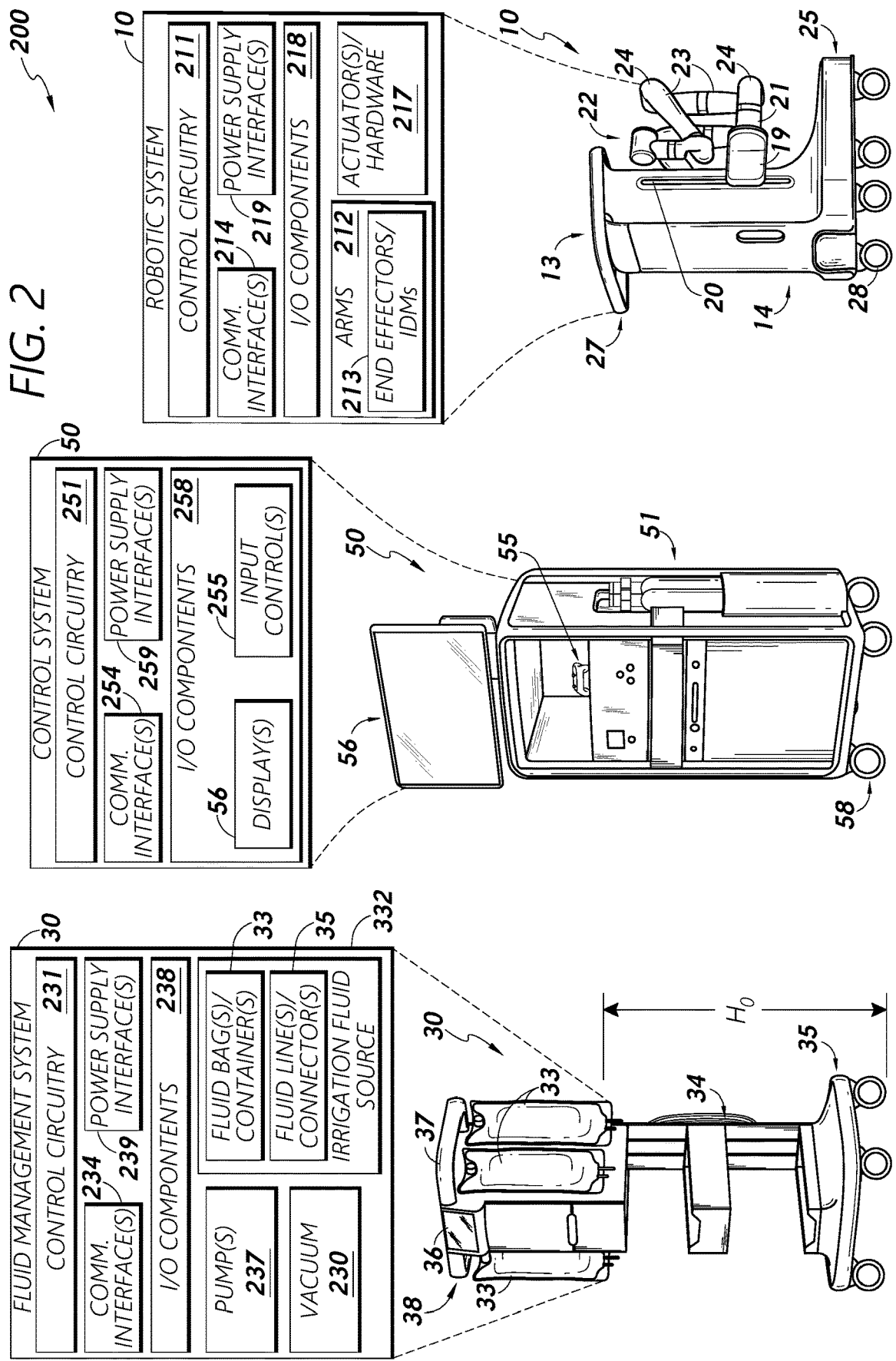
FIG. 2 illustrates medical system components that may be implemented in the medical system of FIG. 1 in accordance with one or more embodiments.

With reference to FIG. 1 and FIG. 2, which shows an example embodiment of the control system 50 of FIG. 1 in accordance with one or more embodiments of the present disclosure, the control system 50 can be configured to provide various functionality to assist in performing a medical procedure. In some embodiments, the control system 50 can be coupled to the robotic system 10 and/or fluid management system 30 and operate in cooperation therewith to perform a medical procedure on the patient 7. For example, the control system 50 can communicate with the robotic system 10 and/or fluid management system 30 via a wireless or wired connection (e.g., to control the robotic system 10, fluid flow from the fluid management system 30, etc.). Further, in some embodiments, the control system 50 can communicate with a needle and/or nephroscope to receive position data therefrom. Moreover, in some embodiments, the control system 50 can communicate with the table 15 to position the table 15 in a particular orientation or otherwise control the table 15. In some embodiments, the control system 50 can communicate with the EM field generator 18 to control generation of an EM field in an area around the patient 7.

FIG. 2 further shows an example embodiment of the robotic system 10 of FIG. 1 in accordance with one or more embodiments of the present disclosure, the robotic system 10 can be configured to at least partly facilitate execution of a medical procedure. The robotic system 10 can be arranged in a variety of ways depending on the particular procedure. The robotic system 10 can include one or more robotic arms 12 configured to engage with and/or control, for example, the scope 32 and/or a percutaneous access catheter 48 to perform one or more aspects of a procedure. As shown, each robotic arm 12 can include multiple arm segments 23 coupled to joints 24, which can provide multiple degrees of movement/freedom. In the example of FIG. 1, the robotic system 10 is positioned proximate to the patient's legs and the robotic arms 12 are actuated to engage with and position the scope 32 for access into an access opening, such as the urethra 65 of the patient 7. When the robotic system 100 is properly positioned, the scope 32 can be inserted into the patient 7 robotically using the robotic arms 12, manually by the physician 5, or a combination thereof. A scope-advancement instrument coupling 11 (i.e., instrument device manipulator (IDM)) can be attached to the distal portion of one of the arms 12c to facilitate robotic control/advancement of the scope 32. Another 12a of the arms may have associated therewith an instrument coupling 19 that is configured to facilitate advancement of the percutaneous-access catheter 48. Any of the percutaneous 40, 48 or direct-entry 32 medical instruments may include one or more working channels through which additional tools, such as lithotripters, basket retrieval devices, forceps, etc., can be introduced into the treatment site.

The robotic system 10 can be coupled to any component of the medical system 100, such as to the control system 50, the table 15, the EM field generator 18, the scope 32, and/or any type of percutaneous-access instrument (e.g., needle, catheter, nephroscope, ect.). In some embodiments, the robotic system 10 is communicatively coupled to the control system 50. For example, the robotic system 10 may be configured to receive a control signal from the control system 50 to perform an operation, such as to position one or more of the robotic arms 12 in a particular manner, manipulate the scope 32, manipulate the catheter 48, and so on. In response, the robotic system 10 can control, using certain control circuitry 211, actuators 217, and/or other components of the robotic system 10, a component of the robotic system 10 to perform the operation. In some embodiments, the robotic system 10 and/or control system 10 is/are configured to receive images and/or image data from the scope 32 representing internal anatomy of the patient 7, namely the urinary system with respect to the particular depiction of FIG. 1, and/or display images based thereon.

With reference to FIG. 2, the robotic system 10 generally includes an elongated support structure 14 (also referred to as a "column"), a robotic system base 25, and a console 13 at the top of the column 14. The column 14 may include one or more arm supports 17 (also referred to as a "carriage") for supporting the deployment of the one or more robotic arms 12 (three shown in FIG. 2). The arm support 17 may include individually-configurable arm mounts that rotate along a perpendicular axis to adjust the base of the robotic arms 12 for better positioning relative to the patient.

The arm support 17 also includes a column interface 19 that allows the arm support 17 to vertically translate along the column 14. In some embodiments, the column interface 19 can be connected to the column 14 through slots 20 that are positioned on opposite sides of the column 14 to guide the vertical translation of the arm support 17. The slot 20 contains a vertical translation interface to position and hold the arm support 17 at various vertical heights relative to the robotic system base 25. Vertical translation of the arm support 17 allows the robotic system 10 to adjust the reach of the robotic arms 12 to meet a variety of table heights, patient sizes, and physician preferences. Similarly, the individually-configurable arm mounts on the arm support 17 can allow the robotic arm base 21 of robotic arms 12 to be angled in a variety of configurations.

The robotic arms 12 may generally comprise robotic arm bases 21 and end effectors 22, separated by a series of linkages 23 that are connected by a series of joints 24, each joint comprising one or more independent actuators 217. Each actuator may comprise an independently-controllable motor. Each independently-controllable joint 24 can provide or represent an independent degree of freedom available to the robotic arm. In some embodiments, each of the arms 12 has seven joints, and thus provides seven degrees of freedom, including "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The robotic system base 25 balances the weight of the column 14, arm support 17, and arms 12 over the floor. Accordingly, the robotic system base 25 may house certain relatively heavier components, such as electronics, motors, power supply, as well as components that selectively enable movement or immobilize the robotic system. For example, the robotic system base 25 can include wheel-shaped casters 28 that allow for the robotic system to easily move around the operating room prior to a procedure. After reaching the appropriate position, the casters 28 may be immobilized using wheel locks to hold the robotic system 10 in place during the procedure.

Positioned at the upper end of column 14, the console 13 can provide both a user interface for receiving user input and a display screen 16 (or a dual-purpose device such as, for example, a touchscreen) to provide the physician/user with both pre-operative and intra-operative data. Potential pre-operative data on the console/display 16 or display 56 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 13 may be positioned and tilted to allow a physician to access the console from the side of the column 14 opposite arm support 17. From this position, the physician may view the console 13, robotic arms 12, and patient while operating the console 13 from behind the robotic system 10. As shown, the console 13 can also include a handle 27 to assist with maneuvering and stabilizing robotic system 10.

The end effector 213 of each of the robotic arms 12 may comprise an instrument device manipulator (IDM), which may be attached using a mechanism changer interface (MCI). In some embodiments, the IDM can be removed and replaced with a different type of IDM, for example, a first type 11 of IDM may manipulate an endoscope, while a second type 19 of IDM may manipulate a catheter. Another type of IDM may be configured to hold an electromagnetic field generator 18. An MCI can include connectors to transfer pneumatic pressure, electrical power, electrical signals, and/or optical signals from the robotic arm 12 to the IDM. The IDMs 213 may be configured to manipulate medical instruments (e.g., surgical tools/instruments), such as the scope 32, using techniques including, for example, direct drives, harmonic drives, geared drives, belts and pulleys, magnetic drives, and the like. In some embodiments, the medical device manipulators 213 can be attached to respective ones of the robotic arms 212, wherein the robotic arms 212 are configured to insert or retract the respective coupled medical instruments into or out of the treatment site.

As referenced above, the system 100 can include certain control circuitry configured to perform certain of the functionality described herein, including the control circuitry 211 of the robotic system 10, the control circuitry 231 of the fluid management system 230, and/or the control circuitry 251 of the control system 50. That is, the control circuitry of the system 100 may be part of the robotic system 10, the fluid management system 30, the control system 50, or some combination thereof. Therefore, any reference herein to control circuitry may refer to circuitry embodied in a robotic system, a fluid management system, a control system, or any other component of a medical system, such as the medical system 100 shown in FIG. 1. The term "control circuitry" is used herein according to its broad and ordinary meaning, and may refer to any collection of processors, processing circuitry, processing modules/units, chips, dies (e.g., semiconductor dies including come or more active and/or passive devices and/or connectivity circuitry), microprocessors, micro-controllers, digital signal processors, microcomputers, central processing units, field programmable gate arrays, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry referenced herein may further include one or more circuit substrates (e.g., printed circuit boards), conductive traces and vias, and/or mounting pads, connectors, and/or components. Control circuitry referenced herein may further comprise one or more, storage devices, which may be embodied in a single memory device, a plurality of memory devices, and/or embedded circuitry of a device. Such data storage may comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware and/or software state machine, analog circuitry, digital circuitry, and/or logic circuitry, data storage device(s)/register(s) storing any associated operational instructions may be embedded within, or external to, the circuitry comprising the state machine, analog circuitry, digital circuitry, and/or logic circuitry.

The control circuitry 211, 231, and/or 251 may comprise a computer-readable medium storing, and/or configured to store, hard-coded and/or operational instructions corresponding to at least some of the steps and/or functions illustrated in one or more of the present figures and/or described herein. Such computer-readable medium can be included in an article of manufacture in some instances. The control circuitry 211/231/251 may be entirely locally maintained/disposed or may be remotely located at least in part (e.g., communicatively coupled indirectly via a local area network and/or a wide area network). Any of the control circuitry 211, 231, 251 may be configured to perform any aspect(s) of the various processes disclosed herein, including the processes shown in FIGS. 7 and 8 and described below.

With respect to the robotic system 10, at least a portion of the control circuitry 211 may be integrated with the base 25, column 14, and/or console 13 of the robotic system 10, and/or another system communicatively coupled to the robotic system 10. With respect to the fluid management system 30, at least a portion of the control circuitry 231 may be integrated with the base 35, column 34, and/or console 38 of the fluid management system 30, and/or another system communicatively coupled to the fluid management system 30. With respect to the control system 50, at least a portion of the control circuitry 251 may be integrated with the console base 51 and/or display unit 56 of the control system 50. It should be understood that any description herein of functional control circuitry or associated functionality may be understood to be embodied in the robotic system 10, the fluid management system 30, the control system 50, or any combination thereof, and/or at least in part in one or more other local or remote systems/devices.

With further reference to FIG. 2, the control system 50 can include various I/O components 258 configured to assist the physician 5 or others in performing a medical procedure. For example, the input/output (I/O) components 258 can be configured to allow for user input to control/navigate the scope 32 and/or catheter 48 within the patient 7. In some embodiments, for example, the physician 5 can provide input to the control system 50 and/or robotic system 10, wherein in response to such input, control signals can be sent to the robotic system 10 to manipulate the scope 32 and/or catheter 48. The control system 50 can include one or more display devices 56 to provide various information regarding a procedure. For example, the display(s) 56 can provide information regarding the scope 32 and/or catheter 48. For example, the control system 50 can receive real-time images that are captured by the scope 32 and display the real-time images via the display(s) 56. Additionally or alternatively, the control system 50 can receive signals (e.g., analog, digital, electrical, acoustic/sonic, pneumatic, tactile, hydraulic, etc.) from a medical monitor and/or a sensor associated with the patient 7, and the display(s) 56 can present information regarding the health or environment of the patient 7. Such information can include information that is displayed via a medical monitor including, for example, information relating to heart rate (e.g., ECG, HRV, etc.), blood pressure/rate, muscle bio-signals e.g., EMG), body temperature, blood oxygen saturation (e.g., $SpO_2$), $CO_2$, brainwaves (e.g., EEG) environmental and/or local or core body temperature, and so on.

To facilitate the functionality of the control system 50, the control system can include various components (sometimes referred to as "subsystems"). For example, the control system 50 can include the control electronics/circuitry 251, as well as one or more power supplies/supply interfaces 259, pneumatic devices, optical sources, actuators, data storage devices, and/or communication interfaces 254. In some embodiments, the control system 50 is movable, while in other embodiments, the control system 50 is a substantially stationary system. Although various functionality and components are discussed as being implemented by the control system 50, any of such functionality and/or components can be integrated into and/or performed by other systems and/or devices, such as the robotic system 10, the fluid management system 30, the table 15, and/or others, for example.

With further reference to FIG. 1, the medical system 100 can provide a variety of benefits, such as providing guidance to assist a physician in performing a procedure (e.g., fluid management status/conditions, instrument tracking, instrument alignment information, etc.), enabling a physician to perform a procedure from an ergonomic position without the need for awkward arm motions and/or positions, enabling a single physician to perform a procedure with one or more medical instruments, avoiding radiation exposure (e.g., associated with fluoroscopy techniques), enabling a procedure to be performed in a single operative setting, providing continuous suction to remove an object more efficiently (e.g., to remove a kidney stone), and so on. For example, the medical system 100 can provide guidance information to assist a physician in using various medical instruments to access a target anatomical feature while minimizing bleeding and/or damage to anatomy (e.g., critical organs, blood vessels, etc.). Further, the medical system 100 can provide non-radiation-based navigational and/or localization techniques to reduce physician and patient exposure to radiation and/or reduce the amount of equipment in the operating room. Moreover, the medical system 100 can provide functionality that is distributed between two or more of the control system 50, the fluid management system 30, and the robotic system 10, which may be independently movable. Such distribution of functionality and/or mobility can enable the control system 50, the fluid management system 30, and/or the robotic system 10 to be placed at locations that are optimal for a particular medical procedure, which can maximize working area around the patient 7 and/or provide an optimized location for the physician 5 to perform a procedure.

The various components of the system 100 can be communicatively coupled to each other over a network, which can include a wireless and/or wired network. Example networks include one or more personal area networks (PANs), local area networks (LANs), wide area networks (WANs), Internet area networks (IANs), cellular networks, the Internet, personal area networks (PANs), body area network (BANs), etc. For example, the various communication interfaces of the systems of FIG. 2 can be configured to communicate with one or more device/sensors/systems, such as over a wireless and/or wired network connection. In some embodiments, the various communication interfaces can implement a wireless technology such as Bluetooth, Wi-Fi, near field communication (NFC), or the like. Furthermore, in some embodiments, the various components of the system 10 can be connected for data communication, fluid exchange, power exchange, and so on via one or more support cables, tubes, or the like.

The control system 50, fluid management, and/or robotic system 10 can include certain user controls 255 (e.g., controls 55), which may comprise any type of user input (and/or output) devices or device interfaces, such as one or more buttons, keys, joysticks, handheld controllers (e.g., video-game-type controllers), computer mice, trackpads, trackballs, control pads, and/or sensors (e.g., motion sensors or cameras) that capture hand gestures and finger gestures, touchscreens, and/or interfaces/connectors therefore. Such user controls are communicatively and/or physically coupled to respective control circuitry.

In some embodiments, a user can manually manipulate a robotic arm 12 of the robotic system 10 without using electronic user controls. For example, during setup in a surgical operating room, a user may move the robotic arms 12 and/or any other medical instruments to provide desired access to a patient. The robotic system 10 may rely on force feedback and inertia control from the user to determine appropriate configuration of the robotic arms 12 and associated instrumentation.

The fluid management system 30 and/or control system 50 can include one or more pumps, flow meters, valve controls, and/or other fluid-/flow-control components (e.g., sensor devices, such as pressure sensors) in order to provide controlled irrigation and/or aspiration/suction capabilities for a medical instrument. In some embodiments, irrigation and aspiration capabilities can be delivered directly to/from a medical instrument through separate cable(s). In some embodiments, the control system 50 can be coupled to the robotic system 10, the table 15, and/or a medical instrument, such as the scope 32 and/or a needle or other percutaneous-access instrument (not shown), through one or more cables or connections (not shown). In some embodiments, the control circuitry 251 of the control system 50 (or the control circuitry 231 fluid management system 30 or the control circuitry 211 of the robotic system to 10) can generate and provide one or more signals to the fluid management system 30 to indicate how high (or low) the irrigation pressure level from the irrigation fluid source 332 can go, wherein such signals can be translated by the fluid management system 30 into irrigation outputs with respect to operation of the pump(s) 237 and/or other flow-control device(s) associated with the irrigation fluid source 332.

Any of the control circuitry 231, the control circuitry 251, and the control circuitry 211 may be configured to control the pump(s) 237 and/or the vacuum 238 to provide irrigation pressure limitation in accordance with aspects of the present disclosure. Any of the medical instruments 32, 40, 48 shown in the system 100 may be attached to the pump(s) 237, which may facilitate irrigation fluid flow. Although FIG. 2 includes the pump(s) 238, in some embodiments, irrigation fluid flow is achieved without the use of pumps, wherein such flow is driven primarily by gravitational potential force. The pump(s) 237 is/are attached to the irrigation source 332, which provides irrigation fluid (e.g., saline solution) to be pumped through one or more of the medical instruments 32, 40, 48 and into the treatment site. In some examples, the pump(s) 237 is/are peristaltic pump(s). In some embodiments, the pump(s) 237 can be replaced with a vacuum that is configured to apply a vacuum pressure to draw the irrigation fluid from the irrigation fluid source 332 and out through the respective coupled medical instrument.

One or more of the percutaneous-access and/or direct-entry instruments implemented in connection with the systems 100, 200 may be fluidly coupled/connected to a vacuum 238 configured to facilitate fluid aspiration. For example, the vacuum 238 can be configured to apply a negative pressure to draw fluid out of the treatment site. The vacuum 238 may be connected to a collection container into which withdrawn fluid is collected. In some examples, aspiration suction may be facilitated by one or more pumps rather than a vacuum. Furthermore, in some embodiments, aspiration is primarily passive, rather than through active suction. Therefore, it should be understood that embodiments of the present disclosure may not include vacuum components.

Case-Specific Irrigation Pressure Control

Figure 3:
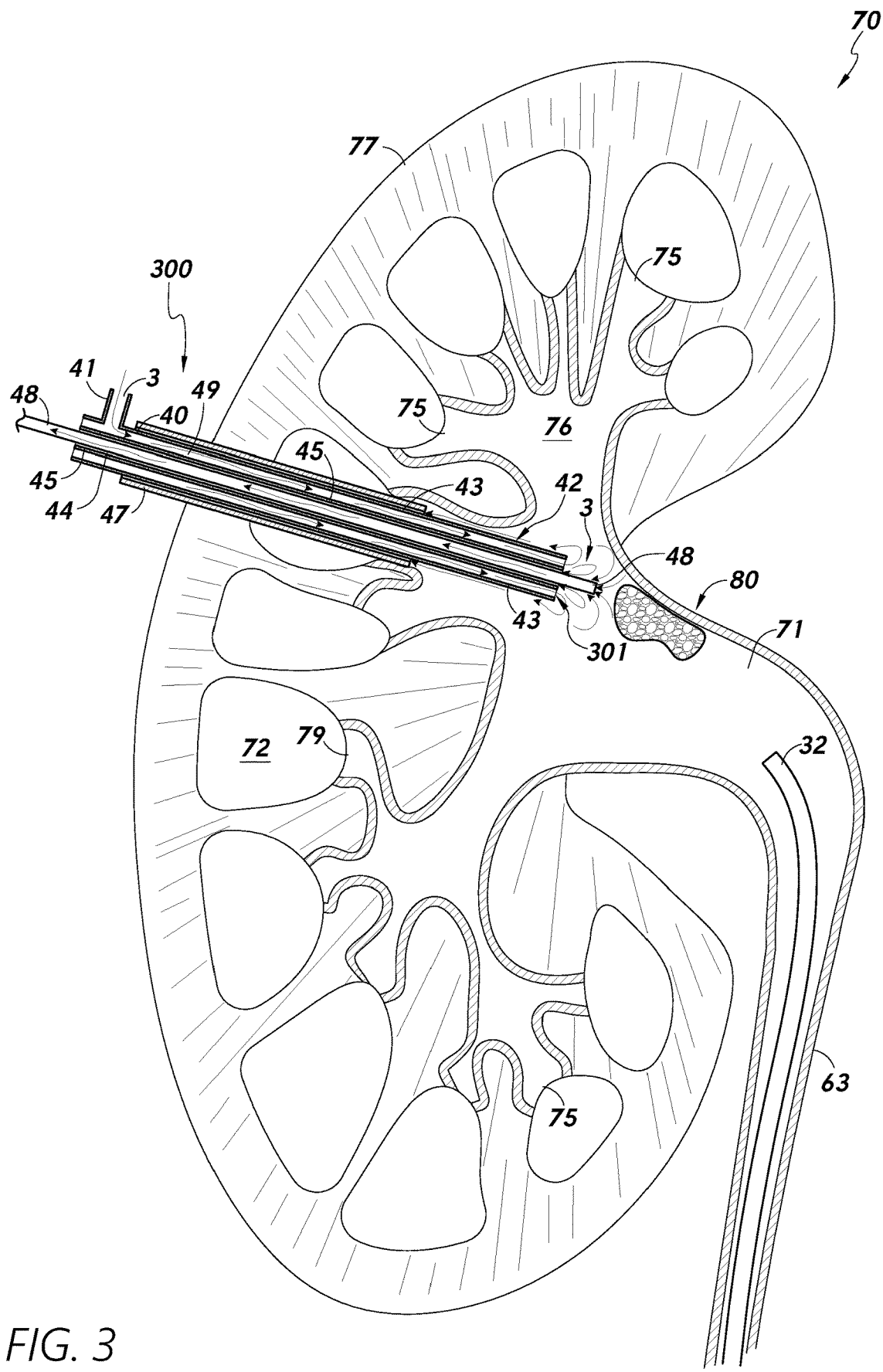
FIG. 3 illustrates a percutaneous-access system disposed in portions of the renal anatomy of a patient in accordance with one or more embodiments.

Various aspects of the present disclosure relate to systems, devices, and methods for managing irrigation fluid flow and pressure with respect to certain medical procedures to provide desirable anatomical distension for effective procedure execution without undue risk of damage to the patient anatomy from over-pressurization. FIG. 3 illustrates a percutaneous-access device/assembly 40 disposed in portions of the renal anatomy 70 of a patient in accordance with one or more embodiments.

A device/system similar to the percutaneous-access device/assembly 40 may be used to provide irrigation (inflow) to a treatment site, such as an internal calyx network of a kidney 70. Fluid irrigation and aspiration, which may be referred to as "fluidics" herein, can represent an important component of certain medical procedures, such as percutaneous nephrolithotomy (PCNL). For example, during PCNL, fluidics may be applied to clear stone dust, small fragments, and thrombus from the treatment site as well as the visual field provided by the medical instrument(s). For example, with respect to the embodiment of FIG. 3, irrigation fluid 3 can be provided through a channel 49 of the percutaneous-access instrument 40. Aspiration (outflow) may exit the treatment site through one or more passive and/or active outflow channels, which may or may not be associated with the percutaneous-access instrument 40. In some embodiments, irrigation and aspiration can both be active.

Embodiments of the present disclosure provide mechanisms for determining and/or implementing maximum and/or minimum irrigation pressure or flow limits with respect to the provision of irrigation fluid to the treatment site through, for example, a percutaneous-access instrument (e.g., nephroscope, catheter, etc.). Such pressure/flow limits may advantageously be determined based on one or more case-specific parameters. The term "case-specific parameter" is used herein according to its broad and ordinary meaning and may refer to any factor, condition, metric, value, configuration, or other parameter relating to a particular patient, procedure, or procedural environment. Case-specific parameters on which an irrigation pressure limit may be based at least in part include, for example, entry angle of the medical instrument providing irrigation; actual or relative height of fluid source; amount of passive and/or active outflow; number of passive and/or active outflow channels; patient position (e.g., modified supine, prone, supine, etc.); irrigation or aspiration flow rate (e.g., instantaneous and/or average flow rate of the irrigation or aspiration over a time interval; the time interval can be, for example, 1.0 seconds, 2.5, second, 5 second, 10 second, 15 seconds, or longer, as well as intervals above and below the listed values); instantaneous fluid pressure associated with the irrigation or aspiration; average fluid pressure associated with the irrigation or aspiration over a time interval; fluid pressure within a medical instrument or patient anatomy, among other possible parameters; presence of a ureteral access sheath, size (e.g., diameter, length, etc.) of a ureteral access sheath; presence of a ureteroscope in a ureteral access sheath; and size of a ureteroscope in a ureteral access sheath.

In some implementations, the case-specific parameter(s) may be determined using one or more sensors associated with one or more of the components of the system (e.g., percutaneous-access and/or direct-entry medical instrument(s)). For example, one or more sensors may be disposed in an irrigation or aspiration fluid channel of a medical instrument. Such sensor(s) can comprise, for example, flow rate sensors, pressure sensors, position sensors, angle sensors, or other sensors for determining case-specific parameter information. Such sensors can be communicatively coupled to control circuitry of one or more system components that is/are configured to determine irrigation pressure limit levels/values based on case-specific parameter(s).

In some embodiments, irrigation pressure limits are determined based at least in part on signals from position sensors configured to provide positional information regarding one or more medical instruments, such as the nephroscope 40, catheter 48, and/or endoscope 32. The position sensors can provide 3-degree-of-freedom (DOF) position information (e.g., x, y, and z coordinates), 5-DOF position information (e.g., x, y, and z coordinates and pitch and yaw angles), or 6-DOF position information (e.g., x, y, and z coordinate and pitch, yaw, and roll angles). Such position sensor(s) can comprise, for example, EM sensors, shape sensing fibers, or other types of position sensors. In some embodiments, one or more accelerometers, gyroscopes, or the like can be used in conjunction in an inertial measurement unit that may be utilized to provide position-related data.

The diagram of FIG. 3 may be representative of a PCNL procedure. The illustrated renal anatomy includes an object disposed in the calyx network of the kidney 70, wherein the object 80 can be any object that is targeted for removal, such as a kidney stone. In the illustrated example, the medical instrument assembly 300 comprises a percutaneous-access laparoscope or nephroscope 40. Although described as a nephroscope below for convenience, it should be understood that the device 40 may be any type of medical instrument. The nephroscope 40 can be inserted percutaneously into the kidney 70 through an access sheath 47. According to some implementations, the access sheath 47 may be placed by first accessing the treatment site with a rigid needle and using a dilator to dilate the percutaneous-access path and place the sheath 47. The nephroscope 40 can include a working channel 44 within an inner shaft/wall 45, though which various tools can be inserted, such as a catheter 48. In some implementations, a lithotripter (such as an ultrasonic lithotripter) may be inserted through the working channel 44 of the nephroscope 40. The nephroscope 40 can also include an optic device (not shown) configured to allow a surgeon to visualize the treatment site.

The catheter 48 may be navigated within the kidney 70 by torqueing the catheter 48 and/or nephroscope 40 towards the object 80. In some implementations, the object/stone 80 may be broken-up using a lithotripter (not shown) and removed in smaller fragments through the percutaneous-access catheter 48. The lithotripter may be advanced to the treatment site through percutaneous or direct entry (e.g., through the nephroscope 40 or through a sheath through which the scope 32 is advanced).

As illustrated with arrows in FIG. 3, irrigation (e.g., saline solution) can be applied to the treatment site (e.g., the kidney 70) through the percutaneous-access instrument 40. The irrigation fluid 3 may enter the nephroscope 40 through an irrigation port 41 and exit through a distal end 301 into the kidney 70. Irrigation can be used to clear stone dust and small fragments from the field of view of, for example, the scope 32 or other image/viewing device to allow the surgeon to visualize the treatment site, as well as to distend the kidney 70 to allow access to the object 80. In the illustrated example, aspiration is also applied to the treatment site through the medical instrument 40. As shown, fluid can be removed from the kidney 70 through the access sheath 47 (e.g., between the outer shaft 43 of the nephroscope and the sheath 47) and/or through the working channel 44 of the nephroscope (e.g., between the inner shaft 45 of the nephroscope and the catheter 48). In some implementations, aspiration may be provided through a channel in a lithotripter. In some instances, aspiration is pulled (actively) through one or more outflow channels and/or permitted to passively flow through one or more outflow channels. For example, active aspiration/suction may be drawn through the catheter 48. In some implementations, fluidics are applied during substantially the entire procedure.

The fluidics applied during the procedure can establish a fluid flow as illustrated by the arrows in FIG. 3. Initially, fluid can flow outward from the distal tip 301 of the nephroscope 40 towards the object 80. Aspiration through the access sheath 47 and/or working channel 44 can cause fluid flow back towards the nephroscope/sheath. As illustrated, in the region of the object 80, the flow may be both directed toward and away from the object 80 with respect to the distal end 301 of the nephroscope 40. Where the available fluid outflow channels are insufficient to remove a flow of fluid equal to the irrigation flow into the treatment site, risks of over-filling the kidney can be present.

During a ureteroscopic lithotripsy procedure, the ureteroscope 32 may enter the kidney 70 through the ureter 63 and use stone-retrieval basket(s) and/or lithotripter(s) to relocate and break down kidney stones, respectively. For example, a lithotripter can be deployed through a working channel of the ureteroscope 32 and used to break the stone 80 into fragments, which may be aspirated through the catheter 48.

Irrigation and/or aspiration can be managed to produce desirable flow characteristics resulting in desirable distension conditions for the target organ/anatomy. In some embodiments, irrigation (inflow) enters the treatment site through a first medical device (e.g., percutaneous-access instrument 40 and/or catheter 48 disposed therein). In some embodiments, the percutaneous-access instrument 40 and/or catheter 48 can be inserted into the treatment site antegrade of an object (e.g., kidney stone) 80 to be removed, whereas another medical instrument (e.g., endoscope) 32 can be inserted into the treatment site retrograde of the object 80. Although FIG. 3 shows the irrigation fluid 3 as provided to the treatment site percutaneously, in some implementations, irrigation may be provided through a medical instrument that accesses the treatment site through direct entry (e.g., via the urinary tract). Any of the percutaneous-access 40, 48 and direct-entry 32 instruments may be robotically controlled as described above with reference to FIGS. 1 and 2. Accordingly, aspects of the methods, devices, and systems described below can be employed robotically in some embodiments.

Generally, the point(s)/channel(s) of inflow (irrigation) may be separate from the point(s)/channel(s) of outflow (aspiration). It may be desirable for the inflow of fluid to be a sufficiently high inflow rate without causing turbulence, thereby allowing the treatment site (e.g., the kidney 70) to fill up with fluid without displacing the stone 80. In some embodiments, the point of outflow (aspiration) may be a single or concentrated point/pathway. Alternatively, a plurality of passive and/or active outflow channels may be provided through which fluid may leave the treatment site. The integral flow of fluid through the outflow channel(s), which may generally be based on the number of outflow channels, the nature of the outflow channel(s) (i.e., passive or active), and the size (e.g., minimum cross-sectional area) of the channel(s). Embodiments of the present disclosure account for the integral outflow of fluid from the treatment site when determining case-specific irrigation pressure limits.

In some embodiments, the irrigation and/or aspiration rate(s) can be modulated to improve stone displacement or stabilization or to intentionally create turbulence so that the irrigation reaches all corners of the treatment site. For example, a gentle alternating cycle of irrigation and aspiration can create a lavage-like effect to preferentially pull large stone debris away from calyces and towards the aspiration site(s). Alternatively, short pulsatile inflow and outflow could be used to create turbulence and ensure that smaller and lighter stone fragments do not settle on the floor of the treatment site, but instead remain floating in the irrigation fluid and eventually are aspirated with the outflow.

The percutaneous-access catheter 48 can be an articulable catheter that is introduced via percutaneous access into the treatment site (e.g., the calyx network of the kidney 70). The catheter 48 can be configured to be able to navigate within the kidney 70. For example, the catheter 48 may be configured to be inserted and retracted into the treatment site and/or to articulate (e.g., bend) therein. In some embodiments, the catheter 48 can include pull-wires for controlling articulation. For example, four pull-wires may be oriented in the four orthogonal directions to enable articulation of the catheter 48. Other methods for permitting articulation of the catheter are also possible. The catheter 48 can include, for example, an aspiration lumen (or channel). The aspiration lumen can be fluidly coupled to a pump/vacuum device (e.g., external pump). The pump/vacuum may generate negative pressure that causes flow from the treatment site into the catheter. The aspiration function may be able to be toggled (e.g., on and off) and adjusted by the user or system. In some embodiments, the aspiration lumen may be used for irrigation as well.

The catheter 48 can provide various functions during an object removal procedure, such as stone stabilization during lithotripsy. For example, if the stone 80 is larger than the aspiration lumen of the catheter, the stone can be held at the distal face of the aspiration lumen, thus stabilizing the stone while it is broken down to dust and smaller fragments. Active aspiration may hold the stone to the distal face of the catheter 48. In some cases, a stone being extracted can substantially seal off the catheter 48, thereby causing the stone to be held by the catheter due to the pressure differential. This may provide the user with a less-mobile target for lithotripsy. Moreover, the catheter 48 can improve visibility of the treatment site by removing stone dust from the kidney. This can provide the user with improved visibility (e.g., continuously adequate visibility), for example, from an imaging device inserted into the treatment site (e.g., camera associated with the scope 32).

The catheter 48 can remove stone dust and fragments, wherein the fluid flow carries fluid and debris into the catheter 48 for removal therethrough. Generally, the debris may be cleared as it is generated (i.e., while the stone is being broken up). The removal of debris via the catheter 48 can take the place of the removal of fragments via ureteroscopic basketing, which can be relatively time consuming due to the difficulty of closing the basket around the stone, and due to the need to remove and re-insert the ureteroscope during each fragment removal. Therefore, using the catheter for stone removal can result in a more efficient removal procedure. Removing stone debris via the catheter can also reduce the risk of the stone fragment(s) injuring tissue compared to certain alternative stone removal methods, such as removal of stones through the ureter.

The catheter 48 can be used in several ways during a procedure. For example, the catheter 48 can be mobile throughout the procedure. The catheter can navigate around the treatment site to target specific stones/fragments in order to constrain them during lithotripsy, while also aspirating dust/debris. As another example, the catheter 48 can be initially stationary during the procedure and the scope 32 can be used to relocate stones to the catheter 48. The stones may be broken down at the 48 catheter. At a later time during the procedure, the catheter 48 may be navigated through the treatment site to pick up remaining debris. As another example, the catheter 48 may be inserted (e.g., percutaneously) only when required, for example, during procedure escalation.

Case-Specific Parameters

As referenced above, the present disclosure relates to systems, devices, and methods for determining and/or implementing irrigation limits based on one or more case-specific parameters. When implemented, a maximum irrigation limit may dictate a threshold level above which irrigation fluid pressure and/or flow may not rise during a procedure. That is, a maximum irrigation limit may prevent fluid pressure and/or flow within a medical instrument configured to provide irrigation through one or more fluid channels thereof from exceeding the maximum irrigation limit threshold/level. Conversely, a minimum irrigation limit may dictate a threshold level below which irrigation fluid pressure and/or flow may not drop during a procedure. For example, a minimum irrigation limit may prevent pressure and/or flow of fluid within a medical instrument configured to provide irrigation through one or more fluid channels thereof from dropping below the minimum irrigation limit threshold/level. Although embodiments are described herein in which implementation of irrigation limits involves preventing irrigation levels from going beyond the irrigation limits, in some implementations, enforcement of irrigation limits may involve providing certain user warnings/notifications relating to such irrigation limits. Such warnings/notifications may be provided without actually impeding/inhibiting the ability of the fluid management system to provide irrigation beyond the limit(s).

Among the case-specific parameters that may provide a basis for irrigation limit determination and/or enforcement is fluid source height (see, e.g., height $H_0$ in FIG. 2 representing or being related with a height of the fluid bags 33 above the ground or other reference). In some embodiments, fluid source height parameters may indicate a relative height of a fluid source relative to a height of the treatment site or other reference, such that the height parameter is indicative of a gravitational potential of the fluid provided from the fluid source to the treatment site.

There are a variety of case-specific parameters that may be implemented in connection with embodiments of the present disclosure, wherein such parameters can drastically affect intrarenal pressure levels and/or inhibit distention of the kidney. Therefore, solutions that do not account for such case-specific variables can be severely limited with respect to the ability to utilize relatively wide irrigation pressure ranges. Among the various case-specific parameters that may be used to determine irrigation pressure limits in accordance with embodiments of the present disclosure include, for example, the number and/or size of passive and/or active flow channels, the angle of passive and/or active outflow channels with respect to the horizon, the height of the patient access point and/or the height of the irrigation fluid port associated with the patient-access device with respect to the irrigation source height, and the particular patient position (e.g., prone, supine, modified supine, Trendelenburg position, etc.).

FIGS. 4A and 4B show side and cross-sectional views, respectively, of a patient 7 in a prone position having a percutaneous-access system 40 disposed at least partially in his/her flank and/or renal anatomy in accordance with one or more embodiments. As apparent in FIG. 4B, the prone position may be desirable for percutaneous access to posterior calyces of kidneys due to the position of the flank 68 of the patient and the access path relative to the position/presence of other critical anatomy 61.

For a PCNL procedure, as shown in FIGS. 4A and 4B, percutaneous access to a posterior calyx 75 of a kidney 70 may result in a nephroscope 40 having a sheath angle of around 45° above the horizon. Therefore, in situations in which the nephroscope 40 and/or instrumentation associated therewith provides passive and/or active aspiration of fluid from the kidney 70, the angle above the horizon may result in a reduced outflow from the kidney due to gravitational pull. With respect to irrigation, the angle $\theta_1$ above the horizon for the percutaneous sheath 42 can have certain effects on irrigation pressure as well. For example, the sheath angle $\theta_1$ may result in a relatively high height of the irrigation port 41 associated with the nephroscope 40, which may further result in reduced irrigation flow/pressure. Therefore, in some cases, the prone position shown in FIGS. 4A and 4B may not provide ideal fluid conditions for the patient. Therefore, case-specific parameter data indicating the particular position of the patient 7 during the procedure may desirably be leveraged in determining, for example, maximum fluid pressure/flow limit(s).

Figures 5A, 5B:
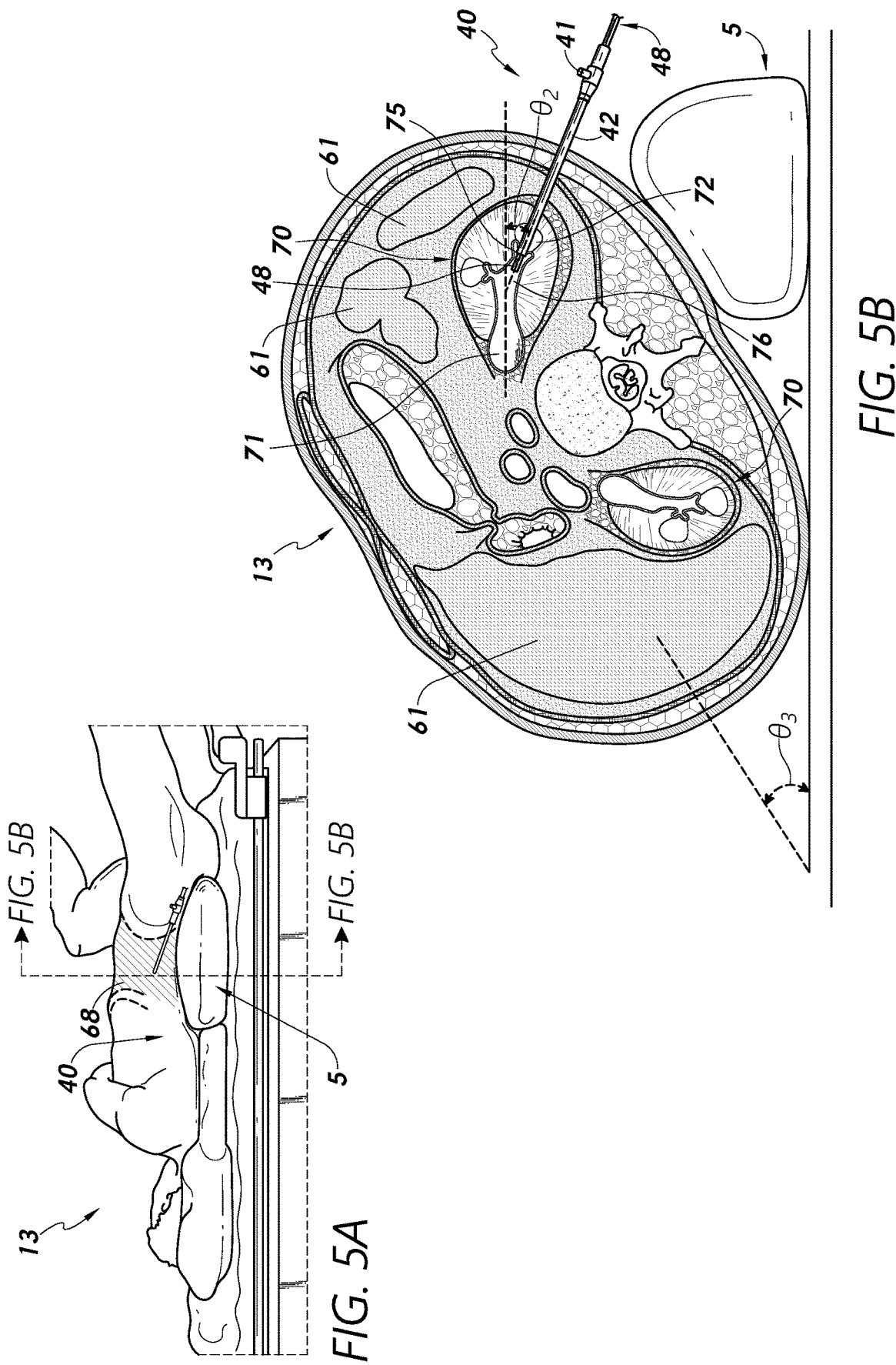
FIGS. 5A and 5B show side and cross-sectional views, respectively, of a patient in a modified supine position having a percutaneous-access system disposed at least partially in his/her renal anatomy in accordance with one or more embodiments.

FIGS. 5A and 5B show side and cross-sectional views, respectively, of a patient in a modified supine position having a percutaneous-access system 40 disposed at least partially in his/her flank and/or renal anatomy in accordance with one or more embodiments. In the modified-supine position, the sheath angle $\theta_2$ may generally be somewhat closer to the horizon than with respect to certain prone procedures due to the orientation of the posterior calyces being generally downward, wherein such downward trajectory is offset at least in part by the tilting of the patient 7 by some angle $\theta_3$ to provide greater exposure for the flank 68 of the patient (e.g., using a pillow or other structure 5 to wedge/support the patient).

As shown in FIGS. 5A and 5B, for percutaneous PCNL procedures in the modified supine position, percutaneous access to a posterior calyx 75 of a kidney 70 may result in a nephroscope 40 having a sheath angle below the horizon, as shown as $\theta_2$ in FIG. 6B. Generally, in a modified supine position, the patient 7 may be propped up using a pillow 5 or similar apparatus to raise the flank 68 of the patients on one side. The prop angle $\theta_3$ may generally be an angle between 0°-45° above the horizon, as shown. Therefore, in situations in which the nephroscope 40 and/or instrumentation associated therewith provide(s) passive and/or active aspiration of fluid from the kidney, the below-horizon sheath angle $\theta_2$ may provide an increased outflow pressure/flow from the kidney 70 due to gravitational pull caused by the relative height difference between the fluid collection container (not shown) and the aspiration collection channel opening(s) associated with the nephroscope 40 (e.g., between the catheter 48 and the nephroscope sheath 42, or between the nephroscope sheath 42 and outer sheath through which the nephroscope 40 is passed). Such increased outflow pressure/flow can be driven mainly by passive outflow when the fluid source (e.g., kidney) is above the fluid outlet (e.g., aspiration channel) due to the negative sheath angle. Consequently, the position generates a positive pressure with respect to the fluid outlet and causes additional fluid outflow compared to more positive sheath angles.

Relative to a case associated with a patient in a prone position, the case shown in FIGS. 5A and 5B with the patient 7 positioned in a modified supine position may be associated with case-specific parameter data relating to aspiration outflow that results in a higher maximum irrigation limit due at least in part to the expected relatively higher passive (and/or active) aspiration outflow compared to the patient in the prone position. For example, according to one example use case, a PCNL procedure performed with a sheath angle of 45° above horizon, such as may be associated with a procedure performed with the patient in the prone position as in FIGS. 4A and 4B, the maximum irrigation pressure limit may be set to a value/threshold at or around 120 mmHg for safety, whereas in the procedure shown in FIGS. 5A and 5B with a sheath angle $\theta_2$ between zero and 45° below the horizon, the maximum irrigation pressure limit may be set to a higher value, such as around 180 mmHg, for example. Therefore, by leveraging case-specific parameter data relating to patient position and/or sheath angle, embodiments of the present disclosure may advantageously allow for a physician to take advantage of significantly higher pressure limits for patients in connection with procedures wherein the patient is in the modified supine position and/or with a below-horizon sheath angle. Such ability to leverage relatively higher maximum pressure limits may advantageously improve the efficacy of the procedure at least in part, such as due to the further distention of the kidney 70 provided by higher irrigation pressures, thereby improving visibility and/or access to one or more areas of the treatment site. For example, improved visibility may be due to the ability to increase suction, which can be implemented without unduly compromising kidney distension due to the increased range of allowable safe irrigation pressure enabled by taking into account one or more case-specific parameters. In solutions not implementing case-specific adjustment/modification to maximum (or minimum) irrigation limits/thresholds, the operating physician may be required to personally choose between competing considerations of considerations of effective visualization (realized from adequate anatomical distention and dust removal), stone holding, and safety. Other positions that may be determined and/or provided as input on which irrigation pressure limits may be based in connection with embodiments of the present disclosure are also contemplated. For example, case-specific parameter information indicating that a patient is positioned in a Trendelenburg position, which involves the body laid supine, or flat on the back, on a 15-30° incline with the feet elevated above the head, may be used to determine irrigation pressure limits. The reverse Trendelenburg position, similarly, places the body supine or back-down on an incline but with the head being elevated.

In some embodiments, determined maximum and/or minimum irrigation limits in accordance with aspects of the present disclosure may be substantially independent of active aspiration through the percutaneous-access instrument/assembly 300. That is, the relationship between the sheath angle $\theta_2$ and the dynamically-determined irrigation pressure limit(s) can assume a fully-occluded catheter 48 with no active aspiration drawn therethrough in some implementations. In some embodiments, active aspiration setpoints are incorporated in the case-specific parameter data upon which irrigation pressure limits are based.

Figure 6:
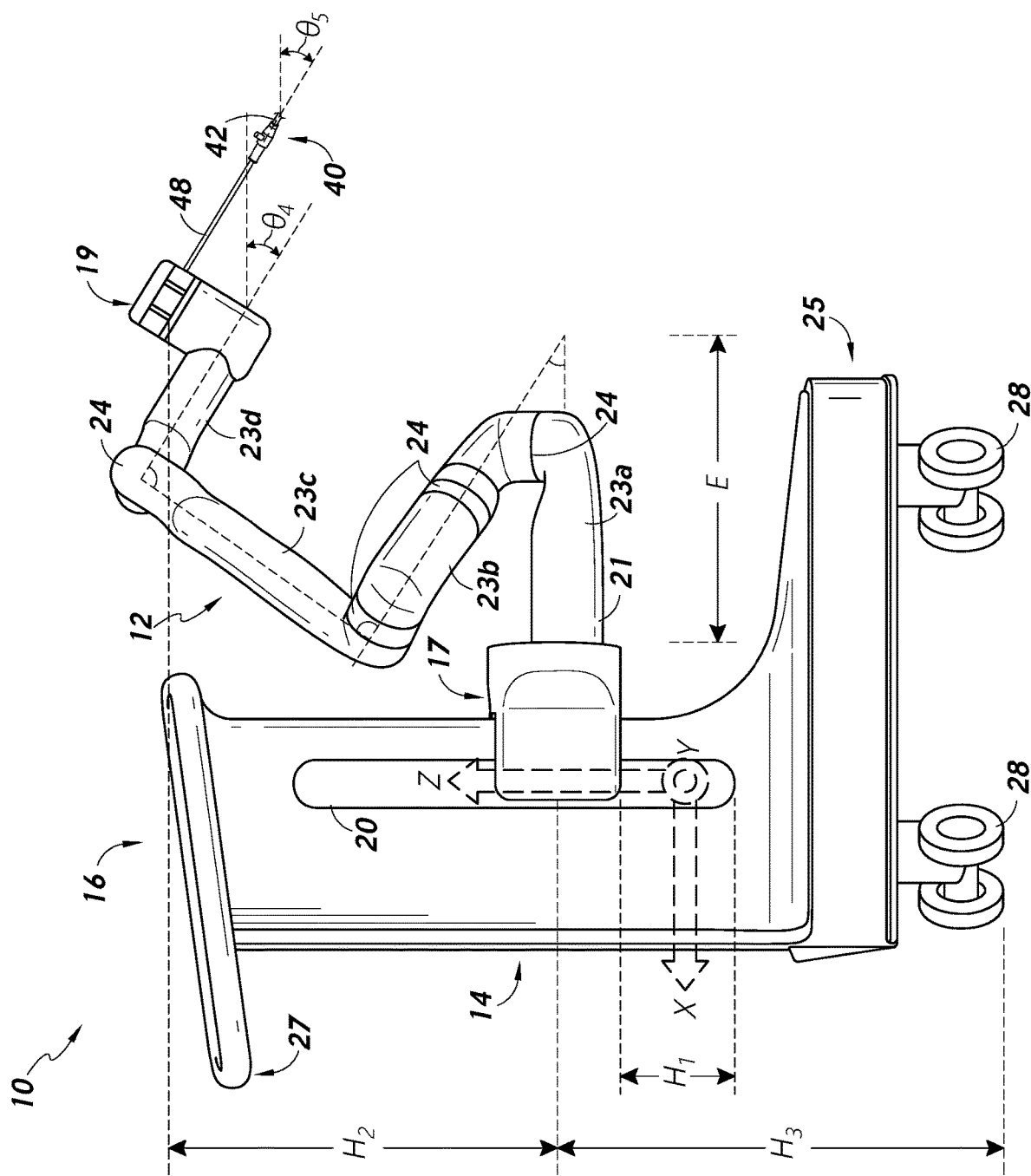
FIG. 6 illustrates an example robotic system that may be implemented in a medical system in accordance with one or more embodiments.

FIG. 6 illustrates an example robotic system that may be implemented in the medical system of FIG. 1 in accordance with one or more embodiments. Embodiments of the present disclosure can utilize robotic system data to determine case-specific variables and adjust maximum and/or minimum irrigation pressure limits dynamically. Among the various case-specific variables that can affect intrarenal pressure and/or inhibit treatment site distention and can serve as bases for integration pressure limit determination are the number and/or volume/flow of passive outflow channels. Such case-specific parameter data can be determined using the robotic system 10, such as by sensing the presence of a ureteral access sheath 42 during a ureteroscopy. Such determination may be based at least in part on proximity sensing, computer vision of the sheath in an endoscope view, or any other means or mechanism. The term "fluid flow" is used herein according to its broad and ordinary meaning and may refer to any representation of fluid volume movement over a period/unit of time.

The positions of the arm segments 23 and/or associated actuators can provide information relating to the position and/or angle of the irrigation device 40 (e.g., percutaneous-access scope/sheath device). For example, due to user variability with respect to the alignment of the sheath 42, the sheath angle $\theta_5$ can be variable across procedures. That is, the sheath angle $\theta_5$ can be considered a case-specific parameter, upon which irrigation limit levels/values may be based in accordance with aspects of the present disclosure. The various angle measurements indicated by actuator position across the various arm segments 23 of the arm 12 can indicate the angle measurement $\theta_5$ of the sheath 42 relative to the horizon. The angle $\theta_4$ of the arm segment 23d, which can be derived by summing the various arm angles of the respective arm segments 23 in some implementations, can provide information indicating the sheath angle $\theta_5$. For example, the arm angle $\theta_5$ combined with information relating to axial rotation of the instrument device manipulator 19 can be used to determine the sheath angle $\theta_5$. Therefore, case-specific parameter data on which irrigation pressure limits may be based in accordance with aspects of the present disclosure can include actuator and/or arm angles as determined and/or provided by the robotic system 10 and/or otherwise determined.

The height of the sheath 40 can further serve as a basis for irrigation pressure limit determination. Such height information may be determined using certain robotic data, such as height data relating to one or more components of the robotic system 10. For example, the height of the sheath 40 may be indicated by the height of the instrument device manipulator (IDM) 19, which is represented by the height $H_2$ between the arm support 17 and the IDM 19 and the height $H_3$ between the arm support 17 and ground, wherein such height may be derived from the position of the arm support 17 and/or arm position/angle information. The height $H_1$ represents a height offset of the arm support 17 within the track 20, which may indicate the height of the sheath at least in part.

In some implementations, the positioning of the robotic arm 12 with the catheter 48 coupled to the device manipulator 19 associated with the arm 12, the catheter 48 being generally coaxial with the sheath 42, may be achieved by first using a needle to puncture the skin and tissue leading to the treatment site (e.g., access through a target papilla into a target calyx of a kidney), after which a guidewire may be passed through and/or along the needle. A dilator can be passed over the guidewire to dilate the percutaneous path to the treatment site. After dilation, a percutaneous sheath can be inserted over the dilator, wherein the catheter 48 can enter the patient through the sheath. The scope 40 may be placed to access the treatment site, and the catheter 48 may be attached to the device manipulator 19 coupled to the arm 12. In some conditions, the robotic arm 12 may be manually positioned to align with, for example, an alignment feature, or otherwise bring the catheter 40 into alignment with the sheath 42. In some implementations, once the robotic arm 12 is in the proper alignment, a snapshot may be taken with respect to the position of the arm 12 and/or manipulator 19 to determine and/or record a position thereof in space. Such position determination/measurement may be made using any position sensing/determination scheme, including electromagnetic position sensing, or based on robotic arm position data.

According to one or more use cases, where the sheath angle $\theta_S$ is below the horizon, intrarenal fluid pressures may be relatively lower, such that adequate distention of the kidney may become a concern. With respect to irrigation solutions that do not incorporate dynamic irrigation pressure limits based on case-specific parameter data, irrigation limits may be set that account for relatively high irrigation/sheath angles. Therefore, irrigation pressure may be limited at a point that is too low, such that the irrigation does not adequately distend the kidney. Such solutions may ensure patient safety but may fail to achieve sufficient distention for procedural efficacy.

In some embodiments, case-specific parameter data may include data relating to the height of the patient. For example, the relative height between the irrigation fluid source and the patient and/or percutaneous-access site on the patient can relate to irrigation and/or aspiration conditions, as described herein. In some embodiments, the height of the patient and/or percutaneous-access site on the patient can be determined and/or inferred based at least in part on robot data indicating the height of a robotic arm of a robotic system that is configured to drive a ureteroscope or other direct-entry instrument or percutaneous-access instrument (e.g., nephroscope or percutaneous-access catheter). For example, the position of the urethra or other opening through which a ureteroscope may be driven can infer the height of the patient and/or the height of certain other areas of the patient's anatomy, which may be inferred based on the patient's position.

The height of one or more portions of the arm 12 may be known based on the actuator/position control of the system. Positional information of the robotic system 10 may indicate an extension distance E the between the distal end of the arm 12 and the arm support 17. The distance E may be used to determine the position and/or angle of the percutaneous-access site, and/or distance between the percutaneous-access site or instrument coupling/manipulator 19 and the fluid collection/source container(s).

In some implementations, the position of the patient may be determined based on robotic system data. For example, the particular arm pose or set of arm poses implemented for a procedure may indicate the position of the patient. That is, one or more arms of the robotic system 10 may have different positions for a procedure on a patient in a prone position compared to a procedure on a patient in a modified supine or other position.

Figure 7:
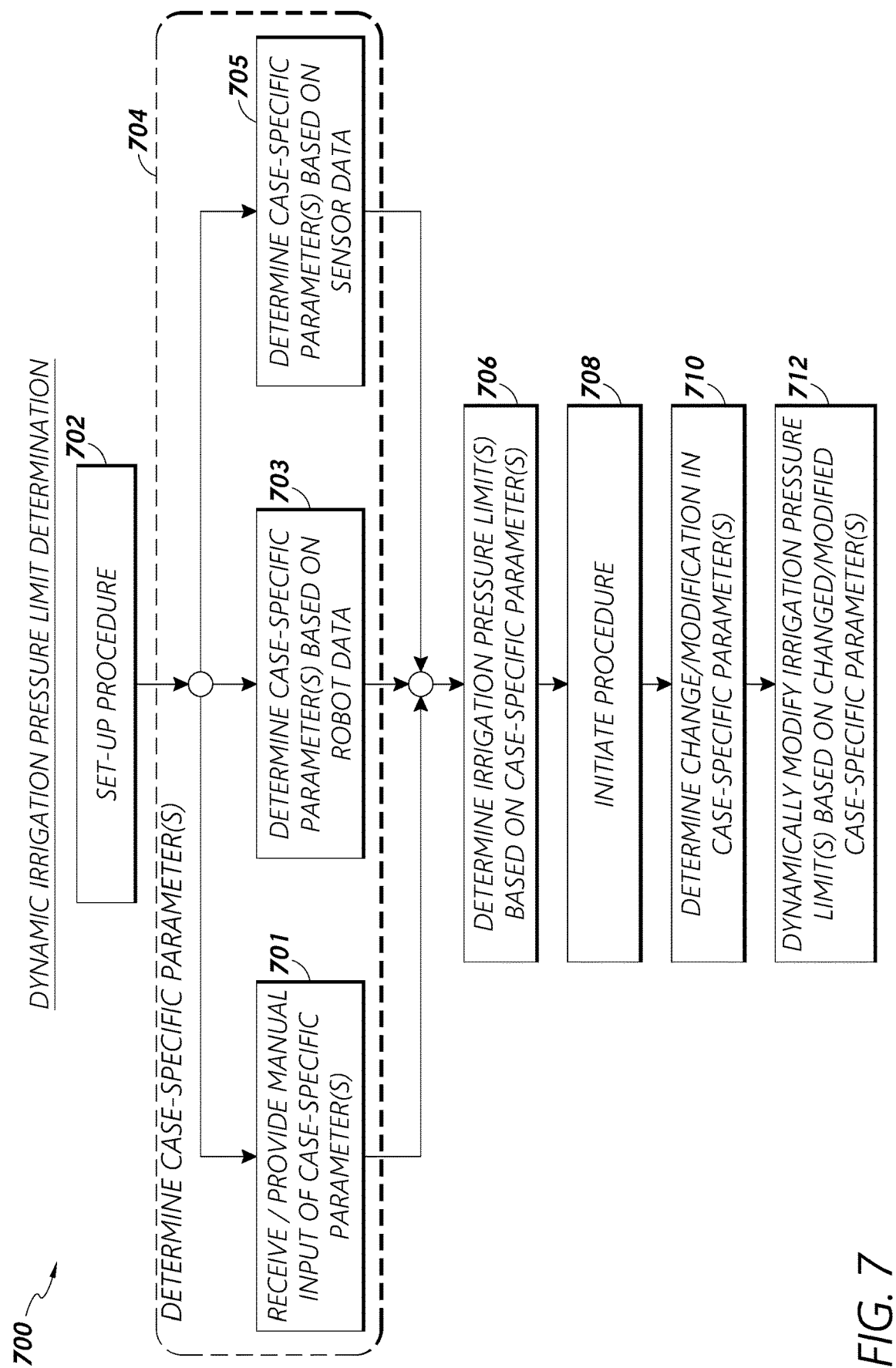
FIG. 7 is a flow diagram illustrating a process for performing percutaneous nephrolithotomy in accordance with one or more embodiments.

FIG. 7 is a flow diagram illustrating a process 700 for performing percutaneous nephrolithotomy in accordance with one or more embodiments. The process 700 may be implemented in connection with a percutaneous kidney-treatment procedure, as described in detail herein, or in connection with any other surgical procedure incorporating irrigation fluid, including, but not limited to, certain gynecological procedures (e.g., involving the use of a morcellator), or other surgical applications. The process 700 may be performed at least in part by the control circuitry of a medical system, such as by control circuitry of one or more of a robotic system, control system, and fluid management system.

As referenced above, according to some implementations of irrigation pressure limiting solutions, a singular irrigation maximum may be applied for a given procedure. For example, according to some solutions, all PCNL procedures may be associated with irrigation pressure maximum of 150 mmHg, without adjustment of the maximum irrigation based on case-specific parameters. Conversely, the process 700 can be implemented to determine and/or apply/enforce irrigation pressure limit(s) that are based on case-specific parameters, such that a plurality/variety of possible irrigation pressure limits/values may be applied for a class of procedure (e.g., PCNL), depending on what case-specific parameters are present and/or input.

At block 702, the process 700 involves setting-up a medical procedure, such as a percutaneous and/or ureteroscopic kidney stone removal procedure. Such set-up may involve positioning a patient on a bed in a desirable/suitable position, positioning one or more robotic arms of a robotic system, coupling one or more irrigation fluid lines from a fluid source to one or more medical instruments, and/or one or more other procedural operations.

At block 704, the process 700 involves determining case-specific parameter(s) or parameter data relevant to the particular procedure. Determining case-specific parameters or parameter data may be performed in any suitable or desirable manner, such as is disclosed herein with any of the embodiments of the present disclosure. For example, the flow diagram of FIG. 7 illustrates certain subprocesses (701, 703, 705) for determining case-specific parameters. For example, at block 701, the process 700 may involve receiving and/or providing manual input of case-specific parameters. The process 700 may involve manually/directly inputting one or more case-specific variables into the system by the physician, technician, or other user. For example, a user interface may be generated and/or presented to the user, wherein the user may be allowed and/or instructed to manually enter parameter information, such as the number of passive and/or active outflow channels, the height (e.g., relative height) of the patient and/or irrigation access area of the patient, the patient position, outflow angle(s), and/or the like, to inform the system of such case-specific parameter values. Output of notifications, warnings, and/or other information in connection with any of the embodiments of the present disclosure may be provided using audible output, LED light(s), and/or other output mechanism(s).

Case-specific parameter data may be input to the system for the purpose of irrigation pressure limit determination in discrete or continuous fashion. For example, in some implementations, case-specific parameter data is input at one or more discrete points in time, such as prior to a procedure. In some implementations, case-specific parameter data may be input to the system sporadically and/or continuously throughout/during a procedure.

At block 703, the process 700 may involve determining case-specific parameters based at least in part on robot data, such as may relate to a robotic cart and/or one or more arms associated therewith, wherein the robotic cart is utilized in performing the medical procedure. At block 705, the process 700 involves determining case-specific parameters based on sensor data associated with one or more medical/surgical instruments and/or anatomy of the patient.

At block 706, the process 700 involves determining irrigation pressure limits based on the determined case-specific parameters. The medical system and/or one or more components thereof (e.g., control circuitry associated with a fluid management system or other control system) may be configured to generate irrigation pressure limits based at least in part on the input/determined case-specific parameter values. Generally, case-specific parameters that may be relied upon for irrigation pressure limit determination may reflect the concept that the higher the pressure and/or flow of aspiration, the higher the inflow irrigation pressure limit may be while still promoting/maintaining patient safety.

The irrigation pressure limit determination may be based at least in part on irrigation instrument (e.g., percutaneous access sheath) angle, which may have a relatively high impact on passive fluid outflow pressures and/or volumes. For example, irrigation instrument/sheath angle may be measured in any suitable or desirable way, such as based on data relating to a robotic arm position during a percutaneous-access catheter alignment sub process that may be implemented in connection with preparation for a procedure.

The determined irrigation pressure limit(s) advantageously reflect a balance of patient safety versus kidney distention. For example, such balancing between safety and distention can be understood with respect to the passive outflow angle(s) in PCNL procedures. At relatively high sheath angles for passive fluid outflow, intrarenal pressures may generally be higher due to the effect of gravity in inhibiting/impeding the passive outflow. Therefore, in such cases, patient safety may represent a substantial/primary concern. Therefore, to ensure patient safety in situations in which case-specific parameters data indicates a relatively high sheath angle for passive fluid outflow, maximum irrigation limits may be relatively lower than in other cases in which sheath angle is lower.

The determination of irrigation pressure limit(s) in connection with block 706 (and/or block 712) may correspond to any suitable or desirable relationship. According to one use case, a maximum irrigation pressure limit may be based on the following relationship:

$$\text{Max\_Irrigation}=C_1*(\text{\# of Channels})+C_2*\text{Angle}+C_3*\text{Height}+C_4*\text{Patient\_Position}+C; \quad (1)$$

wherein the various variables $C_X$ indicate constant values associated with each of the various case-specific parameters, wherein the relationship presented above includes case-specific parameters relating to the number of passive outflow channels, angle of aspiration channel(s), height of patient (e.g., height relative to a reference), fluid source, aspiration channel, or the like, and patient position. In some embodiments, maximum irrigation pressure limits are determined based on sheath angle, but not the remaining case-specific parameters included in the equation (1) above.

In some implementations, case-specific data upon which irrigation pressure limits are based relates to the presence or absence of instrument(s) in the irrigation channel and/or aspiration channel(s), such as laser fibers, baskets, and/or the like, which may have an adverse effect with respect to the amount of irrigation and/or aspiration provided through such channel(s).

In some embodiments, case-specific parameters on which irrigation limits are based relate to one or more physiological characteristics of the patient and/or surgical environment. For example, specific patient tissue stiffness, kidney volume, and/or pressure of the surgical environment may be indicated and/or relied upon to determine the irrigation pressure limit(s). Although certain embodiments are disclosed herein relating to the number of passive and/or active aspiration outflow channels, in some implementations, rather than the number of channels, the sum of flow from all such channels is relied upon as a basis for determining irrigation pressure limits. That is, the total amount (e.g., flow, pressure, volume, etc.) of passive and/or active aspiration outflow may be used as an input for determining maximum and/or minimum irrigation pressure limits.

The recommended/determined maximum irrigation pressure limit(s) may define a generally linear relationship between the measured aspiration outflow angle and the predetermined maximum safe irrigation setpoint. Passive fluid outflow angle (e.g., sheath angle) may be defined in any suitable or desirable manner. For example, in some embodiments, sheath angle is defined as the angle (e.g., in degrees) of the percutaneous-access above or below horizontal/horizon. Generally, with respect to PCNL-type procedures, the expected aspiration sheath angle may range from between −40° to 20° with respect to the horizon. In some embodiments, the determined maximum irrigation pressure may be based at least in part on the following relationship:

$$\text{Rec\_Max\_Irr}=-1.0*\text{Sheath\_Angle}+95; \quad (2)$$

wherein Rec_Max_Irr represents the determined maximum irrigation pressure and Sheath_Angle represents the determined or known aspiration outflow angle, and wherein Rec_Max_Irr is represented in units of mmHg. As represented by equation (2) above, according to some implementations, a recommended maximum irrigation level for aspiration outflow having a horizontal position (i.e., 0° with respect to the horizon) may be approximately 95 mmHg. In some implementations, determined irrigation pressure limit values may be rounded to the nearest 5 mmHg, which may represent a minimum irrigation increment that may be implemented in connection with a fluid management system.

As with any of the embodiments disclosed herein, although certain aspects of the present disclosure are disclosed in the context of maximum irrigation limits, it should be understood that the disclosed principles are applicable to the determination and/or enforcement of minimum irrigation pressure limits as well. Therefore, description of irrigation pressure limits herein should be understood to apply to either or both of maximum and minimum irrigation pressure limits.

At block 708, the process 700 involves initiating the medical/surgical procedure. After the set-up and or initiation of the procedure, the recommended maximum (or minimum) irrigation pressure levels may change dynamically during the procedure, such as in connection with realignment of the irrigation instrument (e.g., percutaneous access sheath and/or catheter).

At block 710, the process 700 involves determining that one or more case-specific parameters have changed or been modified in some manner during performance of the procedure. For example, such determination may be similar in one or more respects to one or more of the sub processes 701, 703, 705 associated with block 704 and described above. In some implementations, the position of the patient may change dynamically during the procedure. Embodiments of the present disclosure allow for dynamic real-time modification of case-specific parameters used for irrigation pressure limit determination, and in turn real-time modification of irrigation pressure limits. In some embodiments, the patient may be operated on while disposed on an at least partially robotically-enabled table, wherein the table operates in a manner that provides data relating to aspects of the patient's position and/or other case-specific parameters. For example, the table may have height adjustment characteristics that provide information relating to the height of the patient and/or percutaneous access instrument(s), which may be relied upon for irrigation pressure limit determination as described in detail above.

At block 712, the process 700 involves dynamically modifying the irrigation pressure limit(s) based on the determined changed and/or modified case-specific parameter(s). The updated irrigation pressure limit(s) can be used during the procedure going forward for a period of time.

Figure 8:
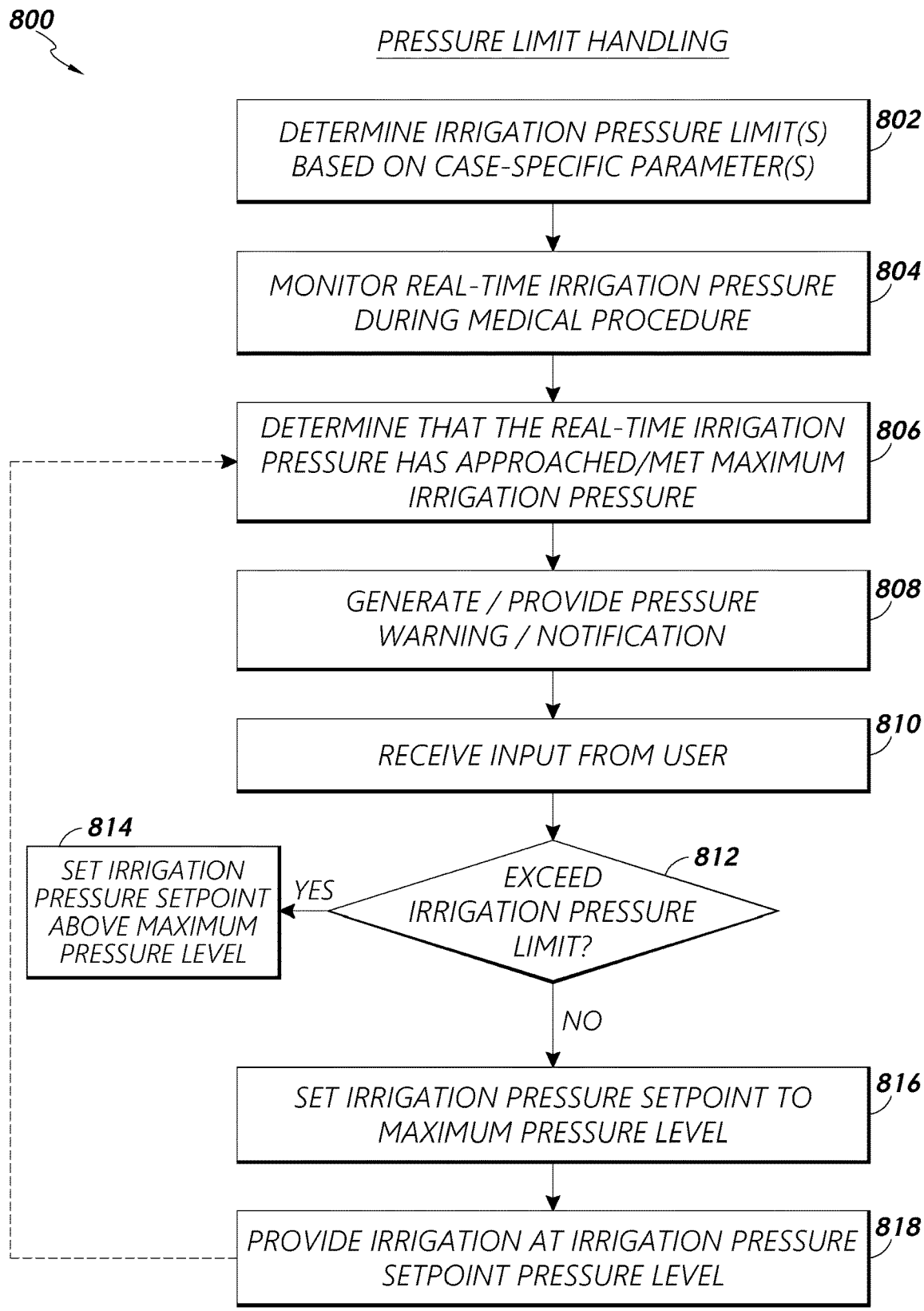
FIG. 8 is a flow diagram illustrating a process for managing fluid pressure in connection with a medical procedure in accordance with one or more embodiments.

FIG. 8 is a flow diagram illustrating a process for managing fluid pressure in connection with a medical procedure in accordance with one or more embodiments. The process 800 may be implemented to determine, for example, a maximum irrigation pressure for a procedure. At block 802, the process 800 involves determining a maximum irrigation pressure based on one or more case-specific parameters, as described in detail herein. Such maximum irrigation pressure limits may provide a variable value that defines a customized irrigation safety limit relating to a maximum recommended safe irrigation pressure. In some implementations, the irrigation pressure limit determination may be tuned to guarantee or promote the maintenance of intrarenal pressure at or below 30 mmHg, which may be considered a maximum clinically-acceptable pressure for certain treatment sites.

At block 804, the process 800 involves monitoring a real-time irrigation pressure implemented in connection with a medical procedure, such as a kidney stone removal procedure.

At block 806, the process 800 involves determining that the real-time irrigation pressure level has approached or met the recommended maximum irrigation pressure level determined at block 802. For example, such determination may be made based on a user entering an irrigation pressure set point that exceeds or approaches the maximum recommended pressure level.

At block 808, the process 800 involves generating and/or providing a notification to a user requesting input with regard to whether the user wishes to exceed the recommended maximum pressure level. For example, such notification may be provided in the form of one or more user interfaces that may have one or more characteristics similar to those shown in FIG. 12 and described in detail below. At block 810, input is received from the user in response to the notification.

If the user provides input indicating a desire to exceed the recommended maximum irrigation pressure, the process 800 proceeds to block 814, where the irrigation pressure setpoint may be set in accordance with the user input directing irrigation pressure above the maximum recommended level. In some implementations, once the user has indicated a desire to exceed the recommended maximum pressure level, the process 800 may not require further affirmations of such in connection with further/future irrigation setpoints that exceed the recommended pressure level(s).

If the user does not provide input indicating a desire to exceed the recommended maximum irrigation pressure, or provides input indicating that the user does not wish to exceed the recommended maximum pressure level, the process 800 proceeds to block 816, where the irrigation pressure level may be set to the recommended maximum, or to a pressure level that approaches the maximum but is less than the maximum. In some embodiments, subsequent changes in irrigation setpoints that are above the recommended maximum irrigation pressure level may trigger provision of the warning notification as in block 808. That is, the process 800 may return to block 808 at any point in response to determination of an irrigation setpoint or irrigation pressure level that is above (or below) a determined maximum pressure level. In some embodiments, the determinants irrigation pressure limit value(s) may be variable between procedures, but may be substantially constant within a given procedure. In alternative embodiments, the irrigation pressure limit value(s) may vary dynamically during an operative period.

Figure 9:
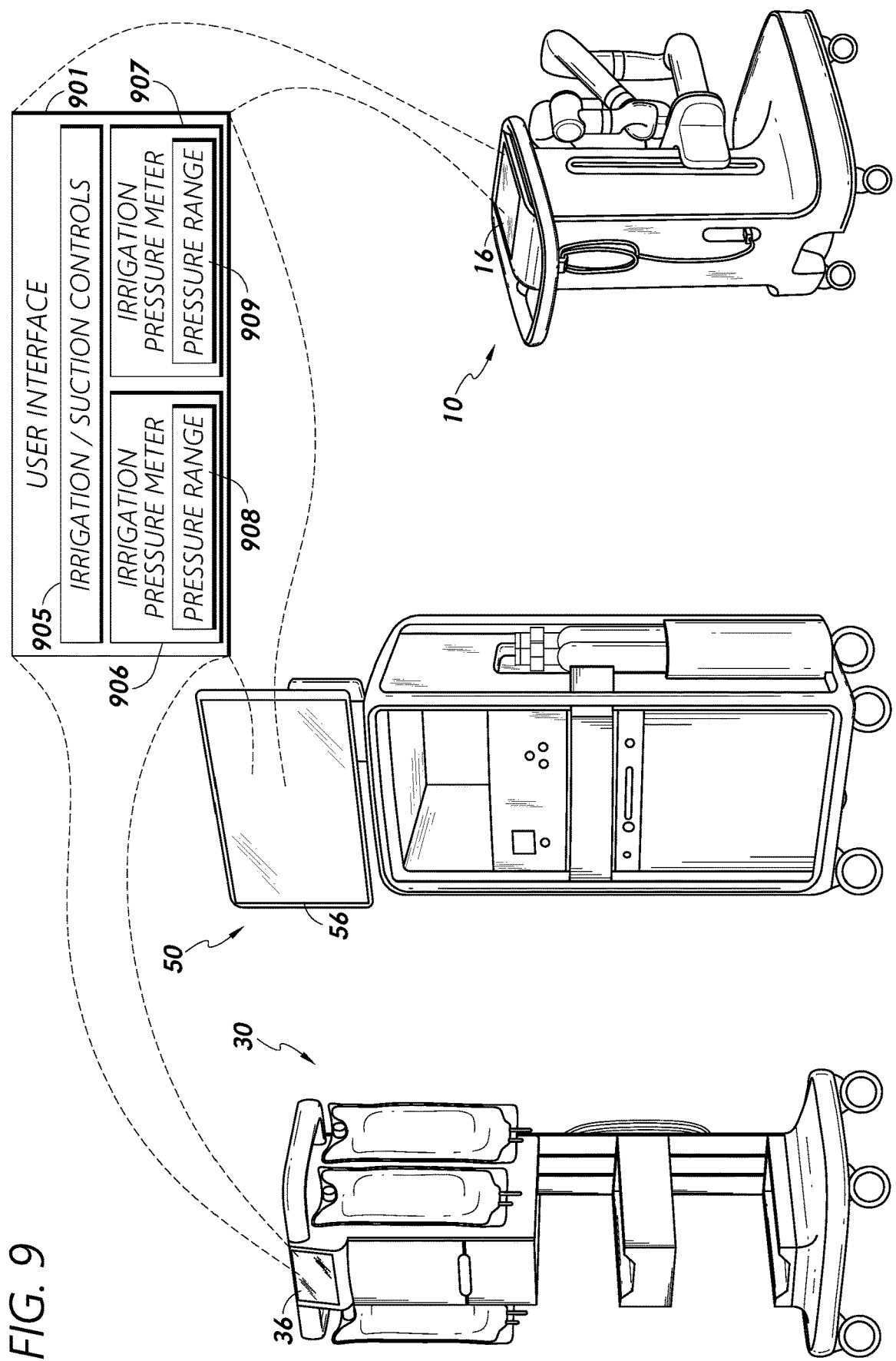
FIG. 9 illustrates medical system components including certain electronic displays configured to present fluid-related interfaces in accordance with one or more embodiments.

FIG. 9 illustrates medical system components including certain electronic displays configured to present fluid-related user interfaces in accordance with one or more embodiments. For example, any of the fluid management interfaces shown in FIGS. 10-12 and described in detail below may be provided to and/or presented on interfaces associated with one or more of the fluid management cart 30, control system 50, and robotic system 10, as described in connection with FIG. 1 above. For example, any of the display devices of the system 100 of FIG. 1 may be configured to display any of the fluid management user interfaces of FIGS. 10-12. In some embodiments, one or more of the interfaces shown in FIG. 9 may allow for a user to input case-specific parameter values, and/or make selections relating thereto as prompted by one or more user interfaces.

One or more of the display devices 36, 56, 16 may include certain fluid-management-related controls 905 (e.g., irrigation and/or suction controls), such as touchscreen controls for providing user input. The display device(s) can be configured to provide data and input commands to the robotic system 10 and/or the fluid management system 30 using integrated display touch controls. The display device(s) can be configured to display graphical user interfaces 901 showing information about a procedure, including irrigation and/or suction control information.

Figure 11:
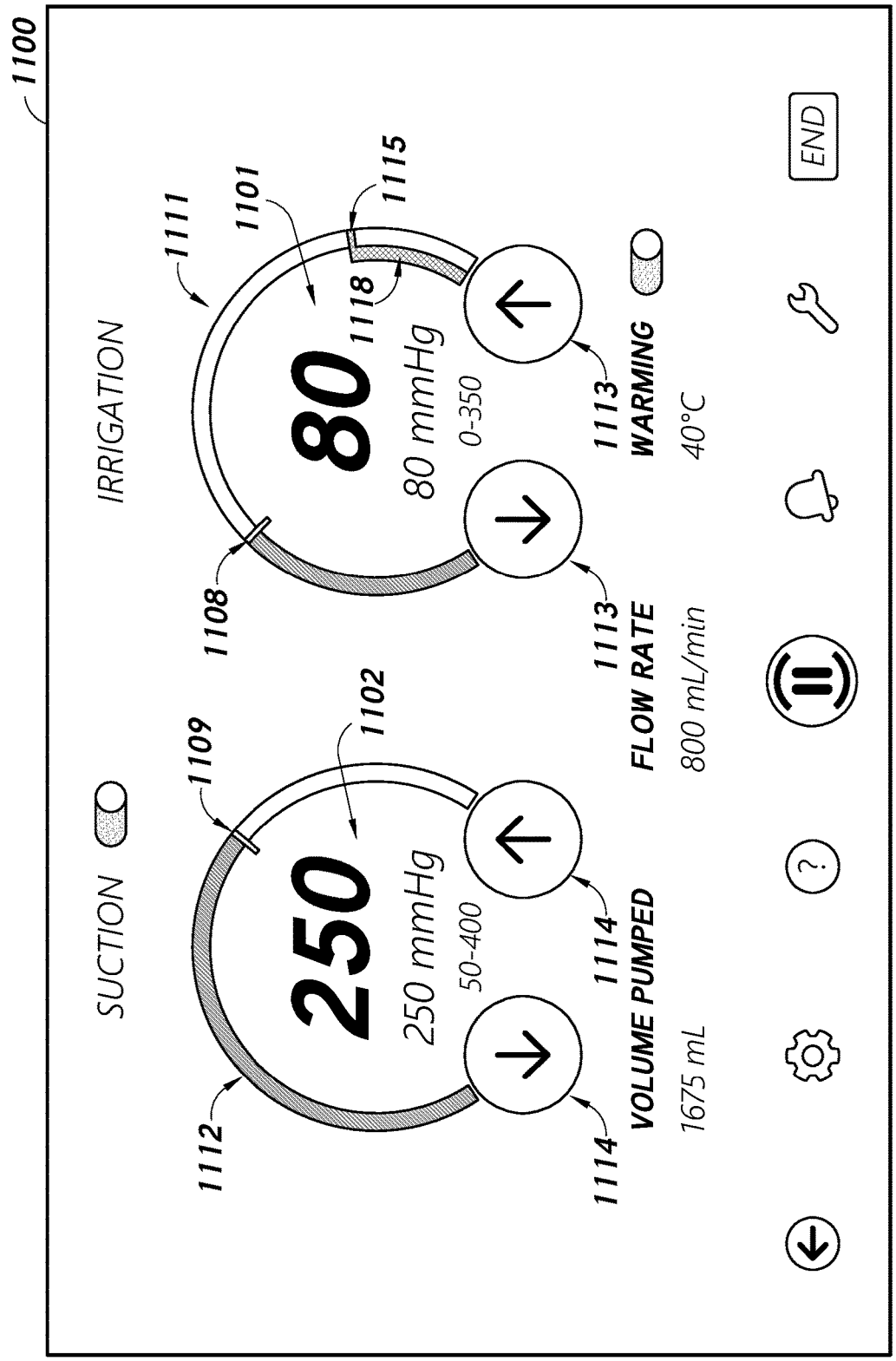
FIG. 11 illustrates an example fluid-management graphical interface in accordance with one or more embodiments.
Figure 12:
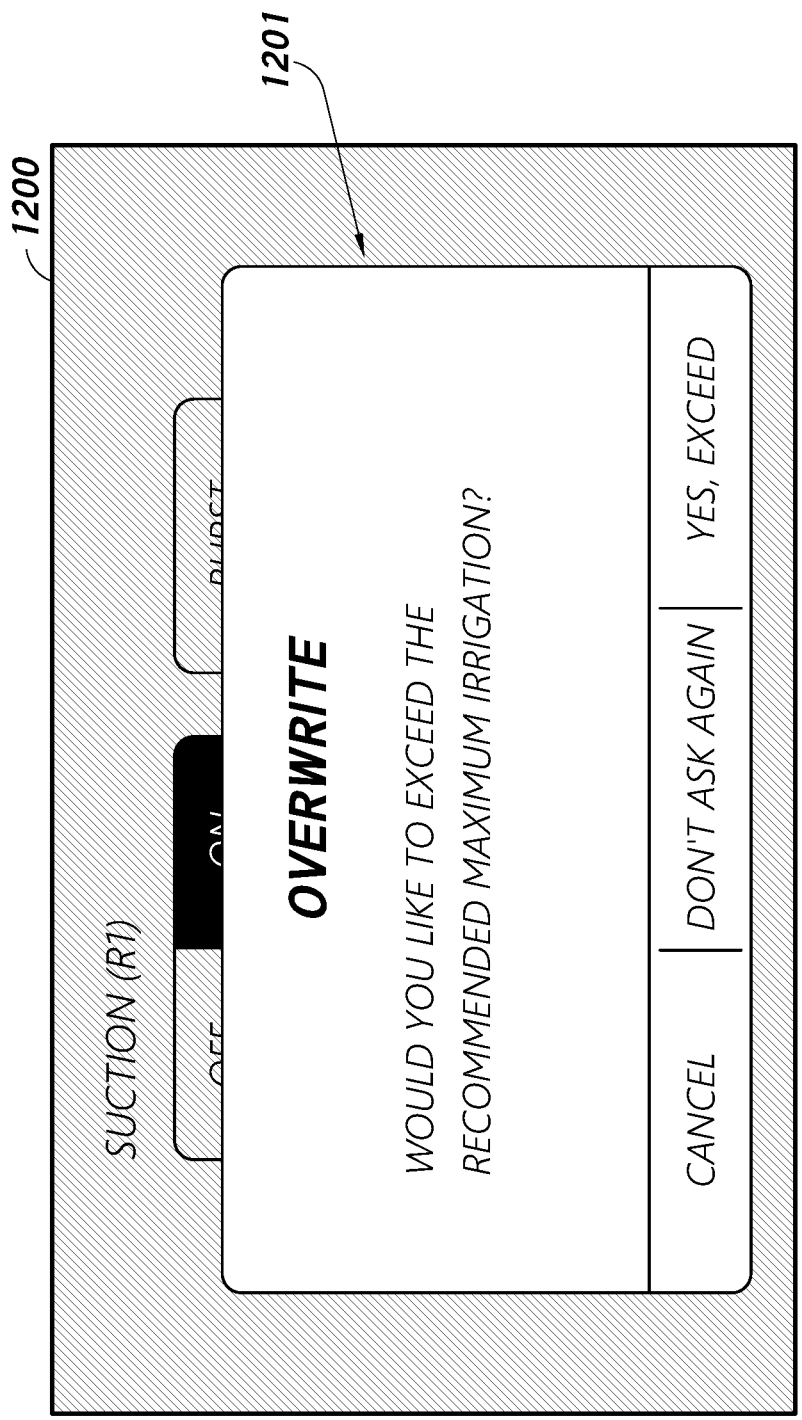
FIG. 12 illustrates an example fluid-management graphical interface in accordance with one or more embodiments.

The user interface component 901 can represent one or more user interfaces (also referred to as "one or more graphical user interfaces (GUI)"). For example, control circuitry of the control system 50, the robotic system 10, and/or the fluid management system 30 may be configured to generate user interface data representing the user interface 901 that includes one or more visualizations to indicate irrigation and/or aspiration fluid conditions. The user interface(s) 901 may include one or more irrigation pressure meter features 906, irrigation pressure range features 908, aspiration pressure meter features 907, and aspiration pressure range features 909, examples of which are shown in FIGS. 10-12.

Figure 10:
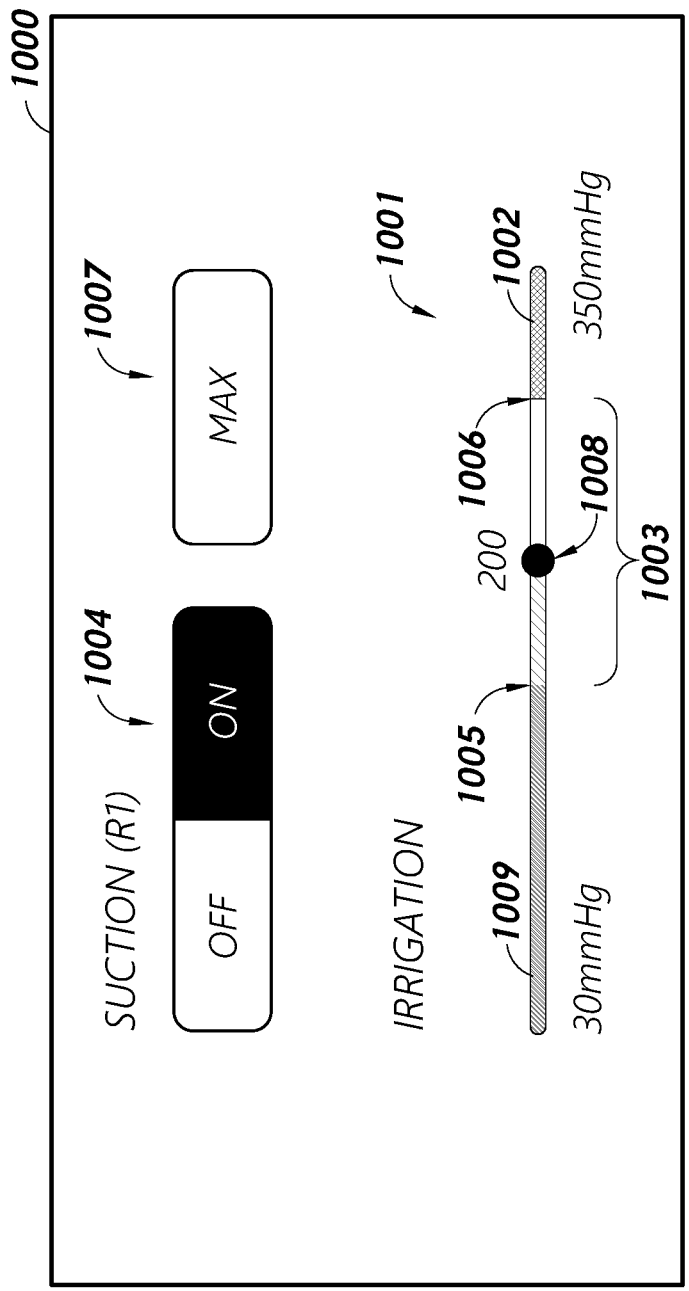
FIG. 10 illustrates an example fluid-management graphical interface in accordance with one or more embodiments.

FIG. 10 illustrates an example fluid-management graphical interface 1000 in accordance with one or more embodiments. The fluid-management graphical interface 1000 includes an irrigation range icon 1000 showing a present/current irrigation level or setpoint 1008. The range 1001 includes an area 1002 above the maximum irrigation pressure level 1006, which may be determined based at least in part on case-specific parameter data, as described in detail herein.

The irrigation range icon 1001 may include a safe (and/or effective) zone or range 1003 within which the irrigation pressure levels are considered safe (and/or effective). For example, the safe zone 1003 may be bounded on respective ends by a minimum pressure level 1005 and a maximum pressure level 1006, either or both of which may be determined based at least in part on one or more case-specific parameters, as discussed in detail herein. In some embodiments, the safe zone 1003 may correspond to irrigation source pressure levels that translate to intrarenal pressures of between about 10 and 30 mmHg, which may provide sufficient kidney distention for a given procedure, while providing a reduced risk of physical injury from over pressurization. Example values for the lower bound 1005 of the irrigation pressure can include, for example, 80 mmHg, 85 mmHg, 90 mmHg, 95 mmHg, 100 mmHg, 105 mmHg, 110 mmHg, 115 mmHg, 120 mmHg, 125 mmHg, 130 mmHg, or any other value. Example values for the upper bound 1006 of the irrigation pressure can include, for example, 140 mmHg, 145 mmHg, 145 mmHg, 150 mmHg, 155 mmHg, 160 mmHg, 165 mmHg, 170 mmHg, 175 mmHg, 180 mmHg, 185 mmHg, 190 mmHg, 195 mmHg, 200 mmHg, or any other value.

The interface 1000 may include a section feature 1004, wherein engagements with the section feature 1004 by the user may allow the user to selectively activate, deactivate, and/or manage active suction in some manner, such as through engagement with a toggle switch for other feature. When active suction is turned on or engaged, relatively large volume of fluid may be aspirated from the target site. Therefore, in situations in which the intrarenal and/or irrigation pressures is/are at or near relatively low pressure levels, activation of active suction through engagement of the feature 1004 can result in undesirable loss of distention at the treatment site. For example, where irrigation pressure is presently at or near the lower bound 1005 of the safe range 1003 prior to initiation of active suction, the effect of the active suction may be to draw the intrarenal pressure below a suitable pressure range for distention purposes (e.g., lower than about 10 mmHg). Furthermore, in situations in which active suction is presently engaged, if the irrigation pressure is at or near the upper bound 1006, clogging of the suction catheter and has decrease in active suction, thereby increasing the intrarenal pressure possibly beyond a safe upper limit (e.g., above about 30 mmHg). Therefore, may be desirable to maintain the present irrigation pressure point 10008 far enough below the upper bound 1006 such that loss of suction will not result in intrarenal pressures exceeding safe limits. In some embodiments, dynamic minimum and maximum irrigation pressure limits may be based on real-time case-specific parameters that incorporate actual pressure level within the treatment site. For example, when were pressure sensors disposed in the treatment site and/or within an area subject to pressure level but can be considered a surrogate of the pressure within the treatment site indicates pressure levels that are at or exceed upper or lower limits, the safe irrigation pressure range 1003 may be dynamically modified to reflect such pressure conditions. For example, such as in response to initiation of active suction and/or reduced active suction (e.g., due to clogging, etc.), actual pressure levels of treatment site may fall or rise below/above certain thresholds, or approach the same, wherein embodiments of the present disclosure provide for dynamic tightening of pressure limit(s) (e.g., raising lower limits and/or lowering upper limits) in response to the case-specific pressure sensor signals. Such dynamic adjustment of irrigation pressure limits may additionally or alternatively be based at least in part on actual detected outflow current and/or pressure levels, which may be determined in any seaboard several men. For example, outflow tracks may include certain flow and/or pressure sensors. As the pressure conditions and/or flow in such outflow channel(s) dynamically change during the procedure, embodiments of the present disclosure can allow for similar dynamic modifications of irrigation pressure limits.

The irrigation pressure setpoint icon 1008 may be engageable by the user to set the desired variation pressure level. In some implementations, the irrigation pressure range slider 1001 may reflect the changed pressure setpoint only after the icon 1008 is released at a given point on the range slider 1001. In some implementations, the user may slide the icon 1008 above the pressure limit 1006 or below the pressure limit 1005 without warning notification interruption, wherein such warning(s) may be generated and/or provided after the setpoint icon 1008 is released/set in the area 1002 above the limit 1006 or the area 1009 below the limit 1005.

FIG. 11 illustrates an example fluid-management graphical interface 1100 in accordance with one or more embodiments. The fluid-management graphical interface 1100 includes an irrigation pressure meter 1111 and a section pressure meter 1112. In irrigation pressure reading or set-point icon 1108 may indicate a present irrigation pressure level or a set pressure level. The setpoint 1108 may be adjustable using certain increase/decrease features 1113. The suction pressure meter 1112 may have an adjustable setpoint 1109 that may be increased or decreased using certain adjustment features 1114, as shown. The region 1118 of the meter 1111 indicates irrigation pressure range that is above the recommended maximum pressure 1115.

The irrigation pressure level may indicate a pressure level associated with the fluid pressure within one or more channel of irrigation instrumentation, rather than providing a direct measurement of intrarenal pressure at the treatment site and some implementations. However, implications about the intrarenal pressure of the treatment site may be provided by the pumped irrigation fluid pressure levels. That is, the input pressure 1101 may be sufficient to manage the fluid conditions of the treatment site according to some implementations.

Any of the user interfaces provided herein may further include functionality for receiving manual case-specific parameter data input from a user. For example, a user interface in accordance with aspects of the present disclosure may provide a mechanism for a user to manually enter the number of aspiration outflow channels, the height of the patient, the patient position, fluid outflow angle(s), and/or other case-specific parameter data, wherein such case-specific parameter data can be used as input in determining irrigation pressure limit(s).

FIG. 12 illustrates an example fluid-management graphical interface in accordance with one or more embodiments.

In some implementations, irrigation pressure limits may be bypassed according to some functionality or mechanism. For example, as shown in the interface 1200, and irrigation limit morning/notification may be provided using one or more user interfaces 1201 warning or otherwise notifying the user that an irrigation limits has been reached or approached. The warning/notification 1201 may query the user with regard to whether the user wishes to allow for the irrigation limit to be breached/exceeded.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A surgical system comprising:
   a medical instrument assembly including an irrigation channel;
   a robotic subsystem including one or more robotic manipulators configured to hold one or more components of the medical instrument assembly;
   an irrigation source fluidly coupled to the medical instrument assembly;
   an irrigation control subsystem configured to control a flow of fluid from the irrigation source to the medical instrument assembly; and
   control circuitry configured to:
      receive data indicating a pose of at least one of the one or more robotic manipulators or at least one of the one or more components of the medical instrument assembly;
      determine an irrigation pressure limit based at least in part on the indicated pose of at least one of the one or more robotic manipulators or at least one of the one or more components of the medical instrument assembly; and
      control the flow of fluid from the irrigation source to the medical instrument assembly in accordance with the irrigation pressure limit.

2. The system of claim 1, wherein the irrigation pressure limit is further determined based on one or more case-specific parameters comprising one or more of the following parameters:
   angle of a sheath associated with the medical instrument assembly;
   amount of aspiration flow;
   whether active suction is implemented;
   relative height of the sheath relative to the irrigation source; and
   patient position.

3. The system of claim 1, wherein:
   the irrigation channel is formed between inner and outer sheaths of a percutaneous-access instrument of the medical instrument assembly; and
   the one or more components comprises a catheter configured to be disposed at least partially within the inner sheath of the percutaneous-access instrument.

4. The system of claim 2, wherein the control circuitry is further configured to:
   determine an angle of a distal portion of one of the one or more robotic manipulators based on robotic subsystem data; and
   determine at least one of the one or more case-specific parameters is-based on the determined angle.

5. The system of claim 2, wherein:
   the medical instrument assembly includes an active suction lumen; and
   the one or more case-specific parameters include a status of the active suction lumen.

6. The system of claim 1, further comprising an electronic display, wherein the control circuitry is further configured to present, using the electronic display, a graphical user interface indicating a pressure range having an upper limit at the irrigation pressure limit.

7. The system of claim 2, wherein the control circuitry is further configured to:
- determine the one or more case-specific parameters continuously during an operative period; and
- update the irrigation pressure limit continuously during the operative period based at least in part on the continuously-determined one or more case-specific parameters.

8. The system of claim 2, wherein:
- the irrigation source comprises a bag of fluid coupled to a support structure; and
- the one or more case-specific parameters include a height of at least one of the bag of fluid and a portion of the support structure relative to a height of one or more components of the medical instrument assembly.

9. The system of claim 2, wherein:
- the medical instrument assembly includes one or more pressure sensors configured to be disposed in a target organ of a patient; and
- the one or more case-specific parameters include a pressure of the target organ based at least in part on a signal from the one or more pressure sensors.

* * * * *